US008119597B2

(12) United States Patent
Sohngen et al.

(10) Patent No.: US 8,119,597 B2
(45) Date of Patent: Feb. 21, 2012

(54) NON-NEUROTOXIC PLASMINOGEN ACTIVATING FACTORS FOR TREATING OF STROKE

(75) Inventors: Mariola Sohngen, Deutschland (DE); Wolfgang Sohngen, Deutschland (DE); Wolf-Dieter Schleuning, Deutschland (DE); Robert Medcalf, Blackburn (AU)

(73) Assignee: Paion GmbH, Aachen (DE)

( * ) Notice: Subject to any disclaimer, the term of this patent is extended or adjusted under 35 U.S.C. 154(b) by 0 days.

(21) Appl. No.: 12/196,785

(22) Filed: Aug. 22, 2008

(65) Prior Publication Data
US 2009/0263373 A1  Oct. 22, 2009

Related U.S. Application Data

(63) Continuation of application No. 10/494,004, filed as application No. PCT/EP02/12204 on Oct. 31, 2002, now abandoned.

(30) Foreign Application Priority Data

Nov. 2, 2001 (DE) .................................. 101 53 601
Dec. 17, 2001 (EP) ..................................... 01130006

(51) Int. Cl.
*A61K 38/36* (2006.01)
*A61K 35/14* (2006.01)
*A61P 7/02* (2006.01)
*C12N 9/50* (2006.01)
*C07K 14/745* (2006.01)

(52) U.S. Cl. ...................... 514/14.9; 514/13.6; 514/13.7; 435/219; 530/380

(58) Field of Classification Search .................. 514/14.9, 514/13.6, 13.7; 435/219; 530/380
See application file for complete search history.

(56) References Cited

U.S. PATENT DOCUMENTS

| 4,766,075 | A | 8/1988 | Goedel et al. |
| 5,094,953 | A | 3/1992 | Anderson et al. |
| 5,223,256 | A | 6/1993 | Stern et al. |
| 5,244,806 | A | 9/1993 | Bang et al. |
| 5,314,818 | A | 5/1994 | Anderson et al. |
| 5,326,700 | A | 7/1994 | Berg et al. |
| 5,500,411 | A | 3/1996 | Martin et al. |
| 5,510,330 | A | 4/1996 | Martin et al. |
| 5,595,736 | A | 1/1997 | Berg et al. |
| 5,648,250 | A | 7/1997 | Niwa et al. |
| 5,676,947 | A | 10/1997 | Martin et al. |
| 5,714,145 | A | 2/1998 | Anderson et al. |
| 5,731,186 | A | 3/1998 | McCaman et al. |
| 5,741,771 | A | 4/1998 | Dawson et al. |
| 5,786,187 | A | 7/1998 | Strickland et al. |

(Continued)

FOREIGN PATENT DOCUMENTS

CA         5 524 573       11/2004

(Continued)

OTHER PUBLICATIONS

Abstract of DE 39 04 580, published Aug. 16, 1990.

(Continued)

*Primary Examiner* — Rosanne Kosson
(74) *Attorney, Agent, or Firm* — Wilmer Cutler Pickering Hale and Dorr LLP

(57) ABSTRACT

The invention concerns the use and the production of non-neurotoxic plasminogen activating factors, derived, for example, from the common vampire *Desmodus rotundus* (DSPA), for therapeutic treatment of stroke in humans. The invention provides a novel therapeutic base for treating stroke in humans.

9 Claims, 10 Drawing Sheets

U.S. PATENT DOCUMENTS

| | | | |
|---|---|---|---|
| 5,827,832 | A | 10/1998 | Sandage, Jr. et al. |
| 5,830,849 | A | 11/1998 | Dixon et al. |
| 5,876,971 | A | 3/1999 | Noeske-Jungblut et al. |
| 5,891,664 | A | 4/1999 | Danø et al. |
| 5,945,432 | A | 8/1999 | Bednar et al. |
| 6,008,019 | A | 12/1999 | Baldus et al. |
| 6,235,279 | B1 | 5/2001 | Martin et al. |
| 6,248,712 | B1 | 6/2001 | Danø et al. |
| 2002/0081294 | A1 | 6/2002 | Bednar et al. |
| 2002/0098179 | A1 | 7/2002 | Brearley et al. |
| 2005/0048027 | A1 | 3/2005 | Söhngen et al. |
| 2006/0135425 | A1 | 6/2006 | Sohngen et al. |
| 2006/0142195 | A1 | 6/2006 | Medcalf |
| 2008/0057050 | A1 | 3/2008 | Sohngen et al. |
| 2008/0213244 | A1 | 9/2008 | Sohngen |
| 2009/0004176 | A1 | 1/2009 | Medcalf et al. |
| 2009/0263373 | A1 | 10/2009 | Sohngen et al. |
| 2010/0272704 | A1 | 10/2010 | Sohngen et al. |

FOREIGN PATENT DOCUMENTS

| | | | |
|---|---|---|---|
| DE | 39 04 580 | | 8/1990 |
| DE | 39 17 949 | | 1/1991 |
| DE | 41 23 845 | | 1/1993 |
| DE | 689 16 532 | T2 | 6/1994 |
| DE | 692 15 537 | T2 | 11/1996 |
| EP | 0 093 619 | | 11/1983 |
| EP | 0 242 836 | | 10/1987 |
| EP | 0273 774 | | 7/1988 |
| EP | 0 352 119 | | 1/1990 |
| EP | 0 352 710 | A2 | 1/1990 |
| EP | 0 386 240 | | 9/1990 |
| EP | 0 618 973 | B1 | 11/1996 |
| EP | 0 383 417 | | 8/1997 |
| EP | 1 308 166 | | 5/2003 |
| EP | 1 308 166 | A | 5/2003 |
| JP | 6506459 | | 7/1994 |
| WO | WO 89/09266 | A1 | 10/1989 |
| WO | WO 91/05048 | | 4/1991 |
| WO | WO 93/12238 | | 6/1993 |
| WO | WO 96/01312 | | 1/1996 |
| WO | WO-97/29188 | | 8/1997 |
| WO | WO 01/51613 | | 7/2001 |
| WO | WO 01/51614 | | 7/2001 |
| WO | WO 03/037363 | | 5/2003 |
| WO | WO 03/037363 | A2 | 5/2003 |
| WO | WO 2004/096267 | | 11/2004 |
| WO | WO 2004/096268 | A3 | 11/2004 |
| WO | WO 2004/098635 | | 11/2004 |
| WO | WO-2005/018564 | | 3/2005 |
| WO | WO 2005/026341 | A3 | 3/2005 |
| WO | WO-2009/049914 | | 4/2009 |

OTHER PUBLICATIONS

Abstract of WO 04/096267, published Nov. 11, 2004.
Abstract of WO 04/098635, published Nov. 18, 2004.
Adams, H. P., et al., "Guidelines for thrombolytic therapy for acute stroke: a supplement to the guidelines for the management of patients with acute ischemic stroke, a statement for healthcare professionals from a special writing group of the stroke council, American Heart Association," Circulation, 94(5):1167-1174 (1996).
Adams, H. P., et al., "Guidelines for the early management of patients with ischemic stroke: a scientific statement from the stroke council of the American stroke association," Stroke, 34:1056-1083 (2003).
Albers, G. W., et al., "Antithrombotic and thrombolytic therapy for ischemic stroke: American college of chest physicians evidence-based clinical practice guidelines (8$^{th}$ edition)," Chest, 133:630S-669S (2008).
Alkawi, A., et al., "Advances in thrombolytics and mechanical devices for treatment of acute ischemic stroke," Neurological Research, 27(1):542-549 (2005).
Atalaya, J. L., et al., "Neurotransmitters and receptors," Journal of Cerebral Blood Flow & Metabolism, 25:S578 (2005).
Baldus, B, et al., Abstract of 0340-6245—Thrombolysis of cerebral clots with desmonds salivary plasminogen activator alphal (DSP Aalphal) compared to alteplase in a rabbit model of embolic, Stroke (1995).
Bhana, N., et al., "Lanoteplase," Biodrugs, 13(3):217-224 (2000).
Brott, T. et al., "Treatment of acute ischemic stroke," The New Engl. J. Med., 343(10):710-722 (2000).
Colman, A., et al., "Post-translational modification of exogenous proteins in 9*Xenopus laevis* oocytes," Biochemical Society Transactions, 12:932-937 (1984).
Desmoteplase (DSPA) publication from Paion from 2007.
DiMasi, J. A., et al., "The price of innovation: new estimates of drug development costs," Journal of Health Economics, 22:151-185 (2003).
Donnan, G. A., et al., "Stroke drug development usually, but not always, animal models," Stroke, 36:2326 (2005).
Fischer, M. et al., "Binding of disease-associated prion protein to plasminogen," Nature, 408:479-483 (2000).
Fisher, M., et al., "Recommendations for standards regarding preclinical neuroprotective and restorative drug development," Stroke, 30:2752-2758 (1999).
Fisher, M., "Use of animal models has not contributed to development of acute stroke therapies con," Stroke, 36:2324-2325 (2005).
Fisher, M., "Enhancing the development and approval of acute stroke therapies, stroke therapy academic industry roundtable," Stroke, 36:1808-1813 (2005).
Fisher, M., et al., "Emerging therapies for acute ischemic stroke new therapies on trial," Stroke, 34:359-361 (2003).
Fisher, M., "The ischemic penumbra: a new opportunity for neuroprotection," Cerebrovasc Dis, 21(2):64-70 (2006).
Furlan, A., et al., "Dose escalation of desmoteplase for acute ischemic stroke (DEDAS): evidence of safety and efficacy 3 to 9 hours after stroke onset," Stroke, 37:1227-1231 (2006).
Furlan, A., et al, "Intra-arterial prourokinase for acute ischemic stroke: the PROACT II study: a randomized controlled trial," JAMA, 282(21):2003-2011 (1999).
"GISSI-2: a factorial randomized trial of alteplase versus streptokinase and heparin versus no heparin among 12,490 patients with acute myocardial infarction. Gruppo italiano per lo studio della sopravvivenza nell'Infarto miocardico," Lancet, 336(8707):65-71 (1990)—Abstract.
Grandjean, C. et al., "Vampire bats yield potent clot buster for ischemic stroke," Journal of Cardiovascular Nursing, 19(6):417-420 (2004).
Grotta, J. C., et al., "Report of the stroke progress review group," National Institute of Neurological Disorders and Stroke, (2002).
Gusto Trial, "An international randomized trial comparing four thrombolytic strategies for acute myocardial infarction," The New England Journal of Medicine, 329(10):673-683 (1993).
Gusto III Study, "A comparison of reteplase with alteplase for acute myocardial infarction," The New England Journal of Medicine, 337(16):1118-1123 (1997).
Hacke, W., et al., "Intravenous desmoteplase in patients with acute ischaemic stroke selected by MRI perfusion-diffusion weighted imaging or perfusion CT (DIAS-2): a prospective, randomized, double-blind, placebo-controlled study," Lancet Neurol, 8:141-150 (2009).
Heymans, et al., "Outcome and one year follow-up of intra-arterial staphylokinase in 191 patients with peripheral arterial occlusion," Thromb. Haemost, 83:666-671 (2000).
Jiao, J. et al., "Characterization of a recombinant chimeric plasminogen activator with enhanced fibrin binding," Biochimica et Biophsica Acta, 1546:399-405 (2001).
Kaste, M., "Thrombolysis in ischaemic stroke—present and future: role of combined therapy," Cerebrovasc. Dis., 11(Suppl. 1):55-59 (2001).
Kaste, M., "Use of animal models has not contributed to development of acute stroke therapies: Pro," Stroke, 36:2323-2324 (2005).
Lees, K. R., et al., "Time to treatment with intravenous alteplase and outcome in stroke: an updated pooled analysis of ECASS, ATLANTIS, NINDS, and EPITHET trials," Lancet, 375:1695-1703 (2010).
Leker, R. R., et al., "Novel therapies for acute ischemic stroke," IMAJ, 8:788-792 (2006).
Lo, E. H., et al., "Mechanisms, challenges and opportunities in stroke," Nature Reviews, Neuroscience, 4:399-415 (2003).

Liu, D., et al., "Tissue plasminogen activator neurovascular toxicity is controlled by activated protein C," Nat. Med., 10:1379-1383 (2004).

Marler, J. R., et al., "Early stroke treatment associated with better outcome: the NINDS tr-PA stroke study," Neurology, 55:1649-1655 (2000).

Meden, P., et al., "Thrombolysis with recombinant desmodus saliva plasminogen activator (rDSPA) in a rat embolic stroke model," Cerebrovasc. Dis., 6:175-194 (4$^{th}$ International Symposium on Thrombolic Therapy (1996).

NINDS group, "Tissue plasminogen activator for acute ischemic stroke," National Institute of Neurological Disorders and Stroke rt-PA Study Group, New England Journal of Medicine, 333:1581-1587 (1995).

Office Action in U.S. Appl. No. 10/184,018 dated Sep. 29, 2004.
Office Action in U.S. Appl. No. 10/184,018 dated Jun. 20, 2005.
Office Action in U.S. Appl. No. 10/571,560 dated Nov. 24, 2009.
Office Action in U.S. Appl. No. 10/555,583 dated Feb. 24, 2009.
Office Action in U.S. Appl. No. 11/878,686 dated Dec. 31, 2008.
Office Action in U.S. Appl. No. 11/878,686 dated Sep. 2, 2009.
Office Action in U.S. Appl. No. 11/878,686 dated Mar. 24, 2010.
Office Action in U.S. Appl. No. 11/313,475 dated Sep. 29, 2004.
Office Action in U.S. Appl. No. 11/313,475 dated Jun. 20, 2005.
Office Action (Interview Summary) in U.S. Appl. No. 11/313,475 dated Mar. 27, 2008.
Office Action in U.S. Appl. No. 10/484,004 dated Oct. 31, 2005.
Office Action in U.S. Appl. No. 10/484,004 dated Nov. 16, 2006.
Office Action in U.S. Appl. No. 10/484,004 dated Mar. 30, 2007.
Office Action in U.S. Appl. No. 10/484,004 dated Jun. 1, 2007.
Office Action in U.S. Appl. No. 10/484,004 dated Jul. 24, 2007.
Office Action in U.S. Appl. No. 10/484,004 dated May 22, 2008.
Office Action in U.S. Appl. No. 10/484,004 dated Jul. 18, 2006.

Peterson, K., "Thrombolytics a field in development," Riv. It. Neurobiologia, 53(1):7-14 (2007).

Read, S.J., "Pharmacological therapy for acute stroke," Curr. Opin. Invest. Drugs, 1(3):329-339 (2000).

Regenberg, A., et al., "The role of animal models in evaluating reasonable safety and efficacy for human trials of cell-based interventions for neurologic conditions," Journal of Cerebral Blood Flow & Metabolism, 29:1-9 (2009).

Ridker, P. M., et al., "Large-scale trials of thrombolytic therapy for acute myocardial infarction: GISSI-2, ISIS-3, and GUSTO-1," Annals of Internal Medicine, 119(6)530-532 (1993).

Saver, J. L., et al., "Alteplase for ischaemic stroke—much sooner is much better," Lancet, 375:1667-1668 (2010).

Soehngen, M., et al., "Drugs for treatment of stroke," in Clinical trials of drugs and biopharmaceuticals, CRC, Lee, C., et al., eds. Ch. 15, 201-235 (2006).

Strbian, D., et al., "Ultraearly thrombolysis in acute ischemic stroke is associated with better outcome and lower mortality," Stroke, 41:712-716 (2010).

Stroke Unit Trialists' Collaboration, "How do stroke units improve patient outcomes?," Stroke, 28(11):2139-2144 (1997).

Sane, et al., Correlation between baseline plasminogen activator inhibitor levels and clinical outcome during therapy with tissue plasminogen activator for acute myocardial infarction, Thromb Haemost, 4:65(3)-275-279 (1991). Abstract.

Tanne, David et al., "Markers of increased risk of intracerebral hemorrhage after intravenous recombinant tissue plasminogen activator therapy for acute ischemic stroke in clinical practice: the multicenter rt-PA acute stroke survey," Circulation, 105:1679-1685 (2002).

Van de Werf, F., et al., "Single-bolus tenecteplase compared with front-loaded alteplase in acute myocardial infarction: the ASSENT-2 double-blind randomized trial," Lancet, 354:716-722 (1999).

van Zonneveld, A, et al, "Autonomous functions of structural domains on human tissue-type plasminogen activator," PNAS USA, 83:4670-4674 (1986).

Zhang, Z., et al., "Adjuvant treatment with neuroserpin increases the therapeutic window for tissue-type plasminogen activator administration in a rat model of embolic stroke," Circulation, 106:740-745 (2002).

Submission to the EPO in German dated Dec. 29, 2005 for European Application No. 01 130 006.8.

Rough English-language translation of Submission to the EPO in German dated Dec. 29, 2005 for European Application No. 01 130 006.8.

U.S. Appl. No. 10/184,018, filed Jun. 28, 2002, Medcalf R, et al.
U.S. Appl. No. 10/555,583, filed Nov. 4, 2005, Söhngen W, et al.
U.S. Appl. No. 10/571,560, filed Mar. 10, 2006, Söhngen W, et al.
U.S. Appl. No. 11/264,088, filed Nov. 2, 2005, Söhngen M, et al.
U.S. Appl. No. 11/311,475, filed Dec. 20, 2005, Medcalf R, et al.
U.S. Appl. No. 11/878,686, filed Jul. 26, 2007, Söhngen M, et al.

"4th International Symposium on Thrombolytic Therapy in Acute Ischemic Stroke" Cerebrovasc Dis. 6: 175-194 (1996).

"Bat Salvia Drug and New MRI Techniques Offer Hope for Acute Stroke Treatment" Neuro Infosource at www.neuroinfosource.com/news, posted Feb. 20, 2004.

"Randomised controlled trial of streptokinase, aspirin and combination of both in treatment of acute ischaemic stroke, Multicentre Acute Stroke Trial-Itlay (MAST-I)", Lancet, vol. 346, No. 8988, pp. 1509-1514 (1995).

"The International Stroke Trial (IST): a randomised trial of aspirin, subcutaneous heparin, both, or neither among 19 435 patients with acute ischaemic stroke", International Stroke Trial Collaborative Group, The Lancet 349: 1569-1581 (1997).

"Thrombolysis in Stroke not justified" SCRIP, No. 2265, p. 26 (1997).

"Thrombolytic Therapy with Streptokinase in Acute Ischemic Stroke, Multicentre Acute Stroke Trial-Europe Study Group", (MAST-E) The New Engl. J. Med. 335: 145-150 (1996).

"Thrombolytics: Therapeutic Class Review" A Pharmacy Healthcare Solutions/An AmerisourceBergen Company publication, ACPE No. 338-999-02-019-H01 (2002).

Adams H et al. "Design of the Trial of Org 10172 in Acute Stroke Treatment (TOAST)" Controlled Clinic Trials 18: 358-377 (1997).

Albers et al., Chest 119:300S 320S (2001).

Baird AE et al.; "Enlargement of human cerebral ischemic lesion volumes measured by diffusion-weighted magnetic resonance imaging" in Ann Neurol. 41:581-589 (1997).

Bakker AHF, et al.: The role of Lysil-Binding site of tissue . . . Journal of Biol. Chem. 270: 12355-12360 (1995).

Baldus B et al. "Thrombolysis of a cerbral clots with *Desmodus* salivary plasminogen activator alpha (ASPA alpha 1) compared to alteplase in a rabbit model of embolic stoke" Thromb. Harmostasis 73: 1398 (1995)—Abstract.

Bode and Renatus: "Tissue-type plasminogen activator: variants and crystal/solution structures . . . " Current Opinion in Structural Biology 7:865-872 (1997).

Butcher KS, et al.; "Refining the perfusion-diffusion mismatch hypothesis" Stroke 36: 1153-1159 (2005).

Cannon CP, et al. "TNK-tissue plasminogen activators in myocardial infraction" Circulation 95:351-356 (1997).

Chalela JA et al. "Early magnetic resonance imaging finding in patients receiving tissue plasminogen activator predict outcome" Insights into the pathophysiology of acute stroke in the thombolysis era. Ann. Neurol. 55: 105-112 (2004).

Chatterton JE et al. "Excitatory glycine receptors containing the NR3 family of NMDA receptor subunits" Nat. 415: 793-798 (2002)—Abstract.

Choi, D., "Glutamate Neurotoxicity and Diseases of the Nervous System", Neuron, vol. 1, pp. 623-634 (1998).

Clark, W. M., et al.; "Recombinant tissue-type plasminogen activator (alterplase) for ischemic stroke 3 to 5 hours after symptom onset," JAMA, 282(21):2019-2026 (1999).

Das S et al. "Increased NMDA current and spine density in mice lacking the NMDA receptor subunit NR3A" Nature 393: 377-381 (1998)—Abstract.

Davidson et al., Biochem. J. 147(1):45 53 (1975)—Abstract.

Diller W, "Persistently Seeking Stroke Solution" in PAION Science News in Stroke 2003, pp. 7-17.

Docagne F et al. "Smad3-dependent induction of plasminogen activator inhibitor-1 in astrocytes mediates neuroprotective activity of transforming growth factor-beta1 against NMDA-induced necrosis" Mol. Cell. Neurosci. 21: 634-344—Abstract, 2002.

Donnan G et al. "Streptokinase for Acute Ischemic Stroke with Relationship to time of Administration" JAMA 267: 961-966 (1996).

Ellis V et al. "Plasminogen activation is stimulated by prion protein and regulated in a copper-dependent manner" Biochemistry 41:6891-6896 (2002).

Epple, G., et al., "Prion protein stimulates tissue-type plasminogen activator-mediated plasmin generation via a lysine-binding site on kringle 2," Journal of Thrombosis and Haemostasis, 2:962-968 (2004).

Emeis, JJ et al. "Hepatic clearance of tissue-type plasminogen activator in rats" Thromb. Haennost. 54(3):661-664 (1985)—Abstract.

Emeis, JJ et al. "Hepatic clearance of tissue-type plasminogen activator in rats" Thromb. Haemost. 54(3):661-664 (1985)—Abstract.

Fauber J "Salvia Drug may help fight strokes" in JSOnline—Milwaukee Journal Sentinel, Feb. 6, 2004 edition.

Fischer M "Recommendations for Advancing Development of Acute Stroke Therapies; Stroke Therapy Academic Industry Roundtable 3" Stroke 34: 1539-1546 (2003).

Fischer M, et al.: Binding of disease-associated prion protein to plasminogen Nature 408: 479-483 (2000).

Furlan AJ "Acute Stroke therapy: Beyond IV tPa" Cleveland Clinic J. of Med 69: 730-734 (2002).

Gay, T. J., "UK Stroke researchers study new clot-busting drug," University of Kentucky Public Relations, (859)257-1754 (2003).

Gill R et al."Pharmocological characterization of RO63-1908 (1-[2-(4-hydroxy-phenoxy)-ethyl]-4-(4-methyl-benzyl)-piperidin-4-01), a novel sinotype-selective N-methyl-D-asparatate antagonist" J Pharmacol. Exp. Ther. 302: 940-948 (2002).

Goeddel DV et al. National Center for Biotechnology Information Accession No. AAA01378 (http://www.ncbi.nlm.nih.gov/entrez/viewer.fcgi?db=protein&val=269380, (1993).

Gotti B et al. "Ifenprodil and SL 82.0715 as cerebral anti-ischemic agents. Evidence for efficacy in models of focal cerebral ischemia" J. Pharmacol. Exp. Ther. 247: 1211-1221 (1988)—Abstract.

Hacke W et al. "Association of outcome with early stroke treatment: Pooled analysis of ATLANTIS, ECASS, and NINDS rt-Pa stroke trial" Lancet 363:768-774 (2004).

Hacke W et al. "Intravenous Thrombolysis with recombinant tissue plasminogen activator for acute hemispheric stroke" JAMA 274: 1017-1025 (1995).

Hacke W et al. "Randomised double-blind placebo-controlled trial of thrombolytic therapy with intravenous alterplase in acute ischaemic stroke (ECASS II)" Lancet 352: 1245-1251 (1998).

Hacke W et al. "The desmoteplase in acute ischemic stroke trial (DIAS),: A phase II MRI-based 9-hour window acute stroke thrombolysis trial with intravenous desmoteplase" Stroke 36: 66-73 (2005).

Higgins et al., "The effect of the one-chain to two-chain conversion in tissue plasminogen activator: characterization of mutations at position 275" Thromb. Res., 57(4):527-39 (1990)—Abstract.

Horrevoets et al. "The specific role of finger and kringle domains of tissue-type plasminogen activator during in vitro fibrinolysis" J. Biol. Chem. 269: 12639-12644 (1994).

International Search Report for PCT/EP2004/004776 (WO 2004/098635) dated Aug. 24, 2004.

International Search Report for PCT/EP2004/010220 (WO 2005/026341) dated Jul. 12, 2005.

International Search Report for PCT/EP2002/12204 (WO 03/037363) dated May 19, 2003.

International Search Report for PCT/EP2004/004626 (WO 2004/096268) dated Dec. 30, 2004.

Karonen JO, et al., "Combined diffusion and perfusion mri with correlation to single-photon emission ct in acute ischemic stroke" Ischemic penumbra predicts infarct growth. Stroke.; 30:1583-1590 (1999).

Kemp JA and McKernan RM NMDA Receptor Pathways as Drug Targets, Nat. Neurosci. 5: s1039-1042 (2002).

Larsen GR et al. "Protein engineering of novel plasminogen activators with increased thrombolytic potency in rabbits relative to Activase" J. Biol. Chem. 266: 8156-8161 (1991).

Lees, KR et al Glycine antagonist (gavestinel) in neuroprotection (GAIN Internatinal) in patients with acute stroke: a randomised controlled trial. GAIN International Investigators. Lancet 355: 1949-1954 (2000)—Abstract.

Lewandowski C. Wiliam Barsan, Treatment of Acute Stroke; in: Annals of Emergency Medicine 37(2):202-206 (2001).

Liberatore GT, et al., "Vampire bat salivary plasminogen activator (desmoteplase): A unique fibrinolytic enzyme that does not promote neurodegeneration" Stroke; 34:537-743 (2003).

Liu D "Tissue plasminogen activator neurovascular toxicity is controlled by activated protein C" Nat. Med. 10:1379-1383 (2004).

Madison E et al. "Serpin-resistant mutants of human tissue-type plasminogen activator" Nature 339: 721-724 (1989).

Madison E. et al. "Amino acid residues that affect interaction of tissue-type plasminogen activator inhibitor 1", Proc. Natl. Acad. Sci.. 87: 3530-3533 (1990).

Madison EL. et al."Restoration of Serine Protease-Inhibitor Interaction by Protein engineering" J. Biol. Chem. 265: 21423-21426 (1990).

Martin U., et al.: "A novel recombinant plasminogen activator" Cardiovascular drug reviews; 11:299-311 (1993).

Matrai et al., "Activation pathway analysis of Rat-{Delta}-{alpha}-chymotrypsin by MD and TMD methods" FEBS Journal 272:s1 (2005)—Abstract.

Molina CA et al., "Thrombolyis-related hemorrhagic infarction: A maker of early reperfusion, reduced infarct size, and improved outcome in patients with proximal middle cerebral artery occlusion" Stroke 33:1551-1556 (2002).

Office Action, U.S. Appl. No. 11/264,088, Jan. 26, 2007.

Office Action, U.S. Appl. No. 11/311,475, Aug. 22, 2006.

Office Action, U.S. Appl. No. 11/311,475, May 31, 2007.

Paoni NF et al. "Making tissue-type plasminogen activator more fibrin specific" Protein Engineering 6: 529-534 (1993).

Paoni, Nicholas F., et al., A slow clearing, fibrin-specific, PAI-1 resistant variant of t-PA (T103N, KHRR 296-299 AAAA), Thrombosis and Haemostasis, 70(2):307-312 (1993).

Pawlak R. Magarinos AM, Melchor J, McEwen B, Strickland S "Tissue plasminogen activator in the amygdala is critical for stress-induced anxiety-like behavior" Nat. Neurosci. 6: 168-174 (2003)—Abstract.

Pawlak R, Nagal N, Urano T, Napiorkowska-Pawlak D, Ihara H, Takada Y, Collen D, Takada A "Rapid, specific and active site-catalyzed effect of tissue-Plasminogen activator on hippocampus-dependent learning in mice" Neuroscience 113: 995-1001 (2002)—Abstract.

Peck P "Bat drug extends stroke treatment time" United Press International (posted Feb. 3, 2004).

Petrovan et al., "Role of residue Phe225 in the cofactor-mediated, allosteric regulation of the serine protease coagulation factor VIIa" Biochemistry, 39(47):14457-63 (2000)—Abstract.

Reddrop C. et al. "Vampire bat salivary plasminogen activator (desmoteplase) inhibits tissue-type plasminogen activator-induced potentiation of excitotoxic injury" Stroke 36:1241-1246 (2005).

Rijken DC et al. "Receptor-mediated endocytosis of tissue type plasminogen activator (t-PA) by liver cells" Thromb. Res.; Supel. X:63-71 (1990)—Abstract.

Ringleb PA et al. "Thrombolytic Therapy within 3 to 6 hours after onset of Ischemic stroke" Stroke 33: 1437-1441 (2002).

Sacco RL et al. "Glycine antagonist in neuroprotection for patients with acute stroke: GAIN Americas: a randomized controlled trial." JAMA 285: 1719-1728 (2001)—Abstract.

Schleuning WD, Alagon A, Boidol W, Bringmann P, Petri T, Kratzschmar J, Haendler B, Langer G, Baldus B, Witt W, et al. Plasminogen activators from the saliva of Desmodus rotundus (common vampire bat): unique fibrin specificity. Ann N Y Acad Sci 667:395-403 (1992).

Smalling RW "Molecular biology of plasminogen activators: what are the clinical implications of drug design?" Thromb. Haemostas. 70:307-312 (1993)—Abstract.

Sottrup-Jensen et al., "Amino-acid sequence of activation cleavage site in plasminogen: homology with 'pro' part of prothrombin" Proc. Natl. Acad. Sci. 72(7):2577-81 (1975)—Abstract.

Tate et al., "Functional role of proteolytic cleavage at arginine-275 of human tissue plasminogen activator as assessed by site-directed mutagenesis" Biochemistry, 26(2):338-43 (1987)—Abstract.

The New England J. of Med. 333(24):1581-1587 (1995).

Tiefenbrunn AJ, et al. "Clinical Pharmacology in patients with evolving myocartinal" Circulation, 71:110-116 (1985).

Tsirka SE, Gualandris A, Amaral DG, Strickland S. Excitotoxin-induced neuronal degeneration and seizure are mediated by tissue plasminogen activator. Nature. 377:340-344 (1995).

van Zonneveld, A., et al.., "Autonomous functions of structural domains on human tissue-type plasminogen activator," Proc. Natl. Acad. Sci. USA, 83:4670-4674 (1986).

Verheyden et al., "A fluorescence stopped-flow kinetic study of the conformational activation of chymotrypsin and several mutants" Protein Science 13:2533-2540 (2004).

Warach S., "Thrombolysis in stroke beyond three hours: Targeting patients with diffusion and perfusion" MRI. Ann. Neurol.;51:11-13 (2001).

Weening-Verhoeff et al.: "Involvement of aspartic and glutamic residues in kringle-2 of tissue-type plasminogen activator in lysine binding, fibrin binding and stimulation of activity as revealed by chemical modification and oligonucleotide-directed mutagenesis," Protein Engineering, 4(2):191-198 (1990).

Witt, W, et al., "Thrombolytic Properties of *Desmodus rotundus* (vampire bat) Salivary Plasminogen Activator in Experimental Pulmonary Embolism in Rats" Blood 79:1213-1217 (1992).

Broderick, J. P., et al., "Treatment of acute ischemic stroke: part I: recanalization strategies," Circulation, 106:1563-1569 (2002).

Ke et al., J. of Biological Chemistry, 272(3):1811-1816 (1997).

Strandberg et al., J. of Biological Chemistry, 270(4):2344-23449 (1995).

Tachias et al., "Variants of tissue-type plasminogen activator which display substantially enhanced stimulation by fibrin," Eur J. of Biological Chemistry, 270(31):18319-19322 (1995).

Schleuning et al., Haemostasis, 31:118-122 (2001).

Madison et al., Science, 262(15):419-421 (1993).

Toschi et al., Eur. J. Biochem., 252:108-112 (1998).

Thomson, Aust. NZ J. Med., 29:533-435 (1999).

Press Release, "Paion sees continued development rationale for desmoteplase based on findings from phase III analysis," 3 pages (Oct. 18, 2007).

Desmoteplase (DSPA), Paion's non-confidential information, 9 pages (Nov. 2007).

Press Release, "Paion is seeking a new US-partner for desmoteplase," 2 pages (Nov. 12, 2007).

C.M. Muller and C.B. Griesinger, "Tissue Plasminogen Activator Mediates Reverse Occlusion Plasticity in Visual Cortex," *Nature Neuroscience* 1(1):47-53 (1998).

esp@cenet summary for DE 689 16 532 T2, published on Aug. 4, 1994.

esp@cenet summary for DE 692 15 537 T2, published on Jan. 9, 1997.

Zhang et al., "Postischemic intracarotid treatment with TNK-tPA reduces infarct volume and improves neurological deficits in embolic stroke in the unanesthetized rat." Brain Res 878:64-71 (2000).

Keyt et al., "A faster-acting and more potent form of tissue plasminogen activator," Proc Natl Acad Sci USA, 91:3670-3674 (1994).

Renatus et al., "Catalytic domain structure of vampire bat plasminogen activator: a molecule paradigm for proteolysis without activation cleavage," Biochem, 36:13483-13493 (1997).

Christou et al., "Timing of recanalization after tissue plasminogen activator therapy determined by transcranial doppler correlates with clinical recovery from ischemic stroke," Stroke 31:1812-1816 (2000).

Barnwell et al., "Safety and efficacy of delayed intraarterial urokinase therapy with mechanical clot disruption for thromboembolic stroke," Am J. Neuroradiol, 15:1817-1822 (1994).

Lee et al., "The changing landscape of ischaemic brain injury mechanisms," Nature, 399(Suppl.):A7-A14 (1999).

Revised Interim Written description Guidelines, 65-66 http://www.uspto.gov/web/offices/pac/writtendesc.pdf, printed on Oct. 30, 2008.

Barnes et al., Neuron, 21:813-825 (1998).

Bringmann et al, J. of Biol. Chem., 270:25596-25603 (1995).

Callaway et al., J. of Nureosci. Methods, 102:53-60 (2000).

Carmeliet et al., Nature, 368:419-424 (1994).

Cartwright, Blood, 43(3):317-326 (1974).

Chen et al., Cell, 91(7):917-925 (1997).

Chen et al., J. of Neurosci., 19(22):9813-9820 (1999).

Frey et al., J. of Neurosci., 16(6):2057-2063 (1996).

Gardell et al., J. of Biol. Chem. 264(30):17947-17952 (1989).

Gardell et al., Circulation, 84(1):244-253 (1991).

Granelli-Piperno et al., J. Exp. Med., 223-234 (1978).

Haung et al., Proc. Natl. Acad. Sci. USA, 93:8699-8704 (1996).

Krätzschmar et al., Gene, 105:229-237 (1991).

Madani et al., The EMBO Journal, 18(11):3007-3012 (1999).

Mellott et al., Arteriosclerosis and Thrombosis, 12(2):212-221 (1992).

Muschick et al., Fibrinolysis, 7:284-290 (1993).

Nicole et al., Nature Medicine, 7(1):59-64 (2001).

Rogove et al., J. of Cell Sci., 112:4007-4016 (1999).

Seeds et al., Science, 270:1992-1994 (1995).

Stewart et al., J. Biol. Chem., 270(29):18292-18299 (1998).

Traynelis et al., Nature, 7(1):17-18 (2001).

Tsirka et al., J. of Neurosci., 17(2):543-552 (1997).

Tsirka et al., Proc. Natl., Acad. Sci., 94:9779-9781 (1997).

Gijn et al., Circulation, 93:1616-1617 (1996).

Wang et al., Nature Medicine, 4(2):228-231 (1998).

Walker et al., J. of Biol. Chem., 276(5):3138-3148 (2001).

Witt et al., Circulation, 90(1):421-426 (1994).

Tsirka et al., Nature, 384:123-125 (1996).

Gething et al., The EMBO J., 7(9):2731-2740 (1988).

Bennett et al., J. of Biol. Chem., 266(8):5191-5201 (1991).

Albers et al., "Desmoteplase 3-9 Hours After Acute Ischemic Stroke: An Update on the DIAS Clinical Trial Program," Poster at the International Stroke Conference (5 panels), Feb. 24, 2010.

Exhibit DD—Adams et al., "Guidelines for the Early management of adult with Ischemic stroke: A guideline from the American Heart Association/American Stroke Association Stroke Council, Clinical Cardiology Council, Cardiovascular Radiology and Intervention Council, and the Atherosclerotic Peripheral Vascular Disease and Quality of care Outcomes in Research Interdisciplinary Working Groups: The American Academy of Neurology affirms the value of this guideline as an educational tool for neurologists," Stroke, vol. 38, pp. 1655-1711 (2007).

Exhibit EE—Hacke et al., "Thrombolysis with Alteplase 3 to 4.5 hours after acute ischemic stroke," The New England Journal of Medicine, vol. 359, pp. 1317-1329 (Sep. 25, 2008).

Exhibit FF—Steiner et al., "The ECASS 3-hour Cohort, Secondary Analysis of ECASS Data by Time Stratification," Cerebrovascular Diseases, vol. 8, pp. 198-203 (1997).

Exhibit GG—The European Stroke Organization (ESO) Executive Committee and the ESO Writing Committee, "Guidelines for management of Ischaemic stroke and Transient Ischaemic Attack 2008," Cerebrovascular Diseases, vol. 25, pp. 457-507 (2008).

Exhibit HH—Del Zoppo et al., "Expansion of the time window for treatment of acute ischemic stroke with intravenous tissue plasminogen activator. A science advisory from the American Heart Association/American Stroke Association," Stroke, vol. 40, pp. 2945-2948 (2009).

Exhibit II—The National Institute of Neurological, Disorders and Stroke tr-PA Stroke Study Group, "Tissue plasminogen activator for acute ischemic stroke," The New England Journal of Medicine, vol. 333, pp. 1581-1587 (1995).

Exhibit JJ—Ingall et al, "Findings From the Reanalysis of the NINDS Tissue Plasminogen Activator for acute Ischemic Stroke treatment trial," Stroke, vol. 35, pp. 2418-242 (2004).

Exhibit KK—Muir, "The Impact of the extended Time window seen in the ECASS III trial on the Guidelines for Stroke management in Europe," European Neurological Journal, vol. 1, pp. 1-5 (2009).

Bath Philip, "Alteplase not yet proven for acute ischaemic stroke," The Lancet, vol. 352, pp. 1238-1239 (Oct. 1998).

Bondaryk et al., "Microheterogeneity, standardization and characterization in glycoprotein drugs," Curr. Drug Discov. vol. 4, pp. 31-32 (2004).

Clark et al., "The rtPA (Alteplase) 0- to 6-hour acute stroke trial part A (A0276g): Results of a double-blind, placebo-controlles, Multicenter Study," Stroke, vol. 31, pp. 811-816 (2000).

Collen et al., "Fibrin-Selective Thrombolytic Therapy for Acute Myocardial Infarction," Circulation, vol. 93, pp. 857-865 (1996).

Degen et al., "The Human Tissue Plasminogen Activator Gene," The Journal of Biological Chemistry, vol. 261, pp. 6972-6985 (1986).

Del Zoppo et al. "Recombinant tissue plasminogen activator in acute thrombotic and embolic stroke," Ann. Neurol., vol. 32(1), pp. 78-89 (1992)—Abstract.

English abstract of EP 0242836 published Oct. 28, 1987.

Forth, Henschler, Rummel and Starke, "Pharmakologie und Toxikologie," Auflage, Wissenschaftsverlag Mannheim, Leipzig, Wien, Zurich, S. 29 (1992)—English Translation.

Chesebro et al., "Thrombolysis in Myocardial Infarction (TIMI) Trial, Phase I: A comparison between intravenous tissue plasminogen activator and intravenous streptokinase. Clinical findings through hospital discharge," Circulation, vol. 76, pp. 142-154 (1987).

International Search Report mailed on Jun. 8, 2009 for International Application No. PCT/EP2008/008871 ISR only was provided.

Jones et al., "Trends in the Treatment of Coronary Disease Today. Selective use of PTCA and Bypass Surgery" Ann. Surg., vol. 197(6), pp. 728-736 (Jun. 1983).

Kase et al., "Cerebral hemorrhage after intra-arterial thrombolysis for ischemic stroke: The PROACT II trial," Neurology, vol. 57, pp. 1603-1610 (2001).

Lee et al., "Local intraarterial urokinase thrombolysis of acute ischemic stroke with or without intravenous abciximab: a pilot study," J. Vasc Interv. Radiol, vol. 13; pp. 769-773 (2002).

Loper-Yunez et al., "Protocol Violations in Community-Based rTPA stroke treatment are associated with Symptomatic Intracerebral Hemorrhage," Stroke, vol. 32, pp. 12-16 (2001).

Lopez-Attalaya et al., "Recombinant Desmodus rotundus Salivary Plasminogen Activator Crosses the Blood-Brain Barrier through a Low-Density Lipoprotein Receptor-Related Protein-Dependent Mechanism without Exerting Neurotoxic Effects," Stroke, vol. 38, pp. 1036-1043 (2007).

Maulaz et al. "Selecting patients for early stroke treatment with penumbra images," Cerebrovasc Dis., vol. 20, suppl 2, pp. 19-24 (2005).

Mebs, "Gifttiere Ein Handbuch fur Biologen, Toxikologen, Arzte und Apotheker," Wissenschaftliche Verlagsgesellschaft mbH, Stuttgart, p. 1-33 (2000)—English translation.

Mutschler, "Arzneimittelwirkungen," 8 Auflage, Wissenschaftliche Verlagsgesellschaft, Stuttgart, S. 512-513 (2001)—English translation.

Nordt et al., "Thrombolysis: newer thrombolytic agents and their role in clinical medicine," Heart, vol. 89; pp. 1358-1362 (2003).

Semba et al., "Alteplase as an alternative to urokinase," JVIR, vol. 11, pp. 279-287 (2000).

"Vampire Bat spit could help stroke victims," Discovery Health Channel at www.health.discovery.com/news, posted Jan. 10, 2003.

Office action in U.S. Appl. No. 11/264,088 dated Jan. 26, 2007.
Office Action in U.S. Appl. No. 11/878,686 dated Jul. 22, 2010.
Office Action in U.S. Appl. No. 12/163,828 dated Oct. 7, 2010.
Office Action in U.S. Appl. No. 10/494,004 dated Jul. 24, 2007.
Office Action in U.S. Appl. No. 10/494,004 dated Jun. 1, 2007.
Office Action in U.S. Appl. No. 10/494,004 dated Mar. 30, 2007.
Office Action in U.S. Appl. No. 10/494,004 dated Nov. 16, 2006.
Office Action in U.S. Appl. No. 10/494,004 dated Jul. 18, 2006.
Office Action in U.S. Appl. No. 10/494,004 dated May 22, 2006.
Office Action in U.S. Appl. No. 10/494,004 dated Oct. 31, 2005.
Office Action in U.S. Appl. No. 11/311,475 dated May 31, 2007.
Office Action in U.S. Appl. No. 11/311,475 dated Aug. 22, 2006.
Interview Summary dated Aug. 6, 2008, for U.S. Appl. No. 10/494,004.
Interview Summary dated Jan. 29, 2008, for U.S. Appl. No. 10/494,004.
Interview Summary dated Mar. 27, 2008, for U.S. Appl. No. 11/311,475.
Interview Summary dated Feb. 23, 2011, for U.S. Appl. No. 12/163,828.

Alexandrov et al., "Speed of intracranial clot lysis with intravenous tissue plasminogen activator therapy," Circulation, vol. 103, pp. 2897-2902 (2001).

Alexandrov et al., "High rate of complete recanalization and dramatic clinical recovery during tPA infusion when continuously monitored with 2-MHz transcranial doppler monitoring," Stroke, vol. 31, pp. 610-614 (2000).

Andersen et al., "Effects of citicoline combined with thrombolytic therapy in a rat embolic stroke model," Stroke, vol. 30, pp. 1464-1471 (1999).

Demchuk et al., "Thrombolysis in brain ischemia (TIBI) transcranial doppler flow grades predict clinical severity, early recovery, and mortality in patients treated with intravenous tissue plasminogen activator," Stroke, vol. 32, pp. 89-93 (2001).

Felberg et al., "Early dramatic recovery during intravenous tissue plasminogen activator infusion," Stroke, vol. 33, pp. 1301-1307 (2002).

Written Opinion mailed on Jun. 8, 2009 for International Application No. PCT/EP2008/008871.

NMDA + DSPA

NMDA + t-PA

NMDA alone

NMDA- Concentration: 50 µM
tPA and DSPA: each 46 µM
Injection site: arrow

DSPA alone t-PA alone

Fig. 9

SEQ ID NO: 2

```
  1 MVNTMKTKLL CVLLLCGAVF SLPRQETYRQ LARGSRAYGV ACKDEITQMT
 51 YRRQESWLRP EVRSKRVEHC QCDRGSNELH QVPSNSCDEP RCLNGGTCVS
101 NKYFSIHWCN CPKKFGGQHC EIDKSKTCYE GNGHFYRGKA STDTMGRPCL
151 PWNSATVLQQ TYHAHRSDAL QLGLGKHNYC RNPDNRRRPW CYVQVGLKPL
201 VQECMVHDCA DFQCGQKTLR EPRFHSTGGE FTTIENQPWF AAIYRRHRGG
251 SGVTYVCGGS LMSPCWVISA THCFIDYPKK EDYIVYLGRS RLNSNTQGEM
301 KFEVENLILH KDYSADTHHN DIALLKIRSK EGRCAQPSRT IQTICLPSMY
351 NDPQFGTSCE ITGFGKENST DYLYPEQLKM TVVKLISHRE CQQPHYYGSE
401 VTTKMLCAAD PQWKEIYPNV TDSCQGDSGG PLVCSLQGRM TLTGIVSWGR
451 GCALKDKPGV YTRVSHFLPW IRSHTKL
```

Fig 10

SEQ ID NO: 1

```
  1 MVNTMKTKLL CVLLLCGAVF SLPRQETYRQ LARGSRAYGV ACKDEITQMT
 51 YRRQESWLRP EVRSKRVEHC QCDRGQARCH TVPVKSCSEP RCFNGGTCQQ
101 ALYFSDFVCQ CPEGFAGKCC EIDTRATCYE DQGISYRGTW STAESGAECT
151 NWNSSALAQK PYSGRRPDAI RLGLGNHNYC RNPDRDSKPW CYVFKAGKYS
201 SEFCSTPACS STCGLRQYSQ PQFHSTGGLF ADIASHPWQA AIFAKHRRSP
251 GERFLCGGIL ISSCWILSAA HCFQERFPPH HLTVILGRTY RVVPGEEEQK
301 FEVEKYIVHK EFDDDTYDND IALLQLKSDS SRCAQESSVV RTVCLPPADL
351 QLPDWTECEL SGYGKHEALS PFYSERLKEA HVRLYPSSRC TSQHLLNRTV
401 TDNMLCAGDT RSGGPQANLH DACQGDSGGP LVCLNDGRMT LVGIISWGLG
451 CGQKDVPGVY TKVTNYLDWI RDNMRP
```

NON-NEUROTOXIC PLASMINOGEN ACTIVATING FACTORS FOR TREATING OF STROKE

CROSS-REFERENCE TO RELATED APPLICATIONS

This application is a continuation of U.S. application Ser. No. 10/494,004, filed on Sep. 24, 2004, now abandoned, and having a §371 filing date of Sep. 24, 2004, which is a U.S. national stage filing of PCT/EP02/12204, filed on Oct. 31, 2002, which claims the benefit of priority from German Application No. 101 53 601.1 and European Application No. 01 130 006.8 filed on Dec. 17, 2001, all of which are incorporated by reference.

BACKGROUND

The invention pertains to the therapeutic use of non-neurotoxic plasminogen activators especially from the saliva of Desmodus rotundus (DSPA) preferentially for the treatment of stroke.

Different clinical pictures are summarized under the term "stroke" which correlate in their clinical symptoms. According to the respective pathogenesis a first differentiation between these clinical pictures in so called ischaemic and haemorrhagic insults is possible.

Ischaemic insults (ischaemia) are characterized in a reduction or interruption of the blood circulation in the brain due to a lack of arterial blood supply. Often this is caused by thrombosis of an arteriosclerotic stenosed vessel or by arterio arterial, respectively, cardial embolisms.

Haemorrhagic insults are based inter alia on the perforation of brain supplying arterias damaged by arterial hypertonia. However, only approximately 20% of all cerebral insults are caused by haemorrhagic insults. Thus, stroke due to thrombosis is much more relevant.

In comparison to other tissue ischaemias the ischaemia of the neuronal tissue is widely accompanied by necrosis of the effected cells. The higher incidence of necrosis in neuronal tissue can be explained with the new understanding of the phenomenon "excitotoxicity" which is a complex cascade comprising a plurality of reaction steps. The cascade is initiated by ischaemic neurons affected by a lack of oxygen which then lose ATP instantaneously and depolarize. This results in an increased postsynaptic release of the neurotransmitter glutamate which activates membrane bound glutamate receptors regulating cation channels. However, due to the increased glutamate release glutamate receptors become over activated.

Glutamate receptors regulate voltage dependent cation channels which are opened by a binding of glutamate to the receptor. This results in a $Na^+$ and $Ca^{2+}$ influx into the cell massively disturbing the $Ca^{2+}$ dependent cellular metabolism. Especially the activation of the $Ca^{2+}$ dependent catabolic enzymes could give reason to the subsequent cell death (Lee, Jin-Mo et al., "The changing landscape of ischaemic brain injury mechanisms"; Dennis W. Zhol "Glutamate neurotoxicity and diseases of the nervous system").

Although the mechanism of glutamate mediated neurotoxicity is not yet entirely understood it is agreed upon that it contributes in a large extent to the neuronal cell death following cerebral ischaemia (Jin-Mo Lee, et al.).

Besides safeguarding vital functions and stabilizing physiological parameter the reopening of the closed vessel has priority in the therapy of acute cerebral ischaemia. The reopening can be performed by different means. The mere mechanical reopening, as e.g. the PTCA after heart attack, so far has not yet led to satisfying results. Only with a successful fibrinolysis an acceptable improvement of the physical condition of patients can be achieved. This can be accomplished by a local application using a catheter (PROCAT, a study with prourokinase). However, despite first positive results this method has not yet been officially approved as a pharmaceutical treatment.

The naturally occurring fibrinolysis is based on the proteolytic activity of the serine protease plasmin which originates from its inactive precursor by catalysis (activation). The natural activation of plasminogen is catalyzed by the plasminogen activators u-PA (urokinase type plasminogen activator) and t-PA (tissue plasminogen activator) occurring naturally in the body. In contrast to u-PA, t-PA forms a so called activator complex together with fibrin and plasminogen. Thus, the catalytic activity of t-PA is fibrin dependent and is enhanced in its presence approximately 550-fold. Besides fibrin also fibrinogen can stimulate t-PA mediated catalysis of plasminogen to plasmin—even though to a smaller extent. In the presence of fibrinogen the t-PA activity is only increases 25-fold. Also the cleavage products of fibrin (fibrin degradation products (FDP)) are stimulating t-PA.

Early attempts of thrombolytic treatment of acute stroke go back to the 1950s. First extensive clinical trials with streptokinase, a fibrinolytic agent from beta-haemolysing streptococci, started only in 1995. Together with plasminogen streptokinase forms a complex which catalyzes other plasminogen molecules into plasmin.

The therapy with streptokinase has severe disadvantages since it is a bacterial protease and therefore can provoke allergic reactions in the body. Furthermore, due to a former streptococci infection including a production of antibodies the patient may exhibit a so called streptokinase resistance making the therapy more difficult. Besides this, clinical trials in Europe (Multicenter Acute Stroke Trial of Europe (MAST-E), Multicenter Acute Stroke Trial of Italy (MAST-1)) and Australia (Australian Streptokinase Trial (AS7)) indicated an increased mortality risk and a higher risk of intracerebral bleeding (intracerebral haemorrhage, ICH) after treating patients with streptokinase. These trials had to be terminated early.

Alternatively, urokinase—also a classical fibrinolytic agent—can be applicated. In contrast to streptokinase it does not exhibit antigenic characteristics since it is an enzyme naturally occurring in various body tissues. It is an activator of plasminogen and independent of a cofactor. Urokinase is produced in kidney cell cultures.

Extensive experience on therapeutic thrombolysis is available for the tissue type plasminogen activator—the so called rt-PA—(see EP 0 093 619, U.S. Pat. No. 4,766,075), which is produced in recombinant hamster cells. In the 90s several clinical trials were performed world-wide using t-PA—with acute myocardial infarction as the main indication—leading to partially non-understood and contradictory results. In the so called European Acute Stroke Trial (ECASS) patients were treated within a time frame of 6 hours after the onset of the symptoms of a stroke intravenously with rt-PA. After 90 days the mortality rate as well as the Barthel-index were examined as an index for the disability or the independent viability of patients. No significant improvement of the viability was reported but an—even though not significant—increase of mortality. Thus, it could be concluded, a thrombolytic treatment with rt-PA of patients being individually selected according to their respective case history immediately after the beginning of the stroke could possibly be advantageous. However, a general use of rt-PA within the time frame of 6 hours after the onset of stroke was not recommended since an application during this time increases the risk of intracerebal haemorrhage (ICH) (C. Lewandowski C and Wiliam Barsan, 2001: Treatment of Acute Stroke; in: Annals of Emergency Medicine 37:2; S. 202 ff.).

The thrombolytic treatment of stroke was also subject of a clinical trial conducted by the National Institute of Neurologic Disorder and Stroke (so called NINDS rtPA Stroke Trial) in the USA. This trial concentrated on the effect of intravenous rt-PA treatment within only three hours after the onset of the symptoms. Patients were examined three months after the treatment. Due to the observed positive effects of this treatment on the viability of patients, rt-PA treatment within these limited time frame of three hours was recommended although the authors found a higher risk for ICH.

Two further studies (ECASS II Trial: Alteplase Thrombolysis for Acute Noninterventional Therapy in Ischaemic Stroke (ATLANTIS)) examined whether the positive effects of rt-PA treatment within three hours after the onset of stroke could be repeated even with a treatment within six hours time. However, this question could not be answered affirmatively since no improvement of the clinical symptoms or any decrease in mortality was observed. The higher risk for ICH remained.

Those partially contradictory results have led to a high caution in the use of rt-PA. Already 1996 a publication of the American Heart Association pointed out the strong skepticism among doctors with respect to thrombolytic treatment of stroke; whereas there is no such skepticism with respect to fibrinolytica in the therapy of myocardical infarct (van Gijn J. MD, FRCP, 1996-Circulation 1996, 93: 1616-1617).

A rational behind this skepticism was firstly given in a summary of all stroke trials published 1997 (updated in March 2001). According to this review all thromtolytica treatments (urokinase, streptokinase, rt-PA or recombinant urokinase) resulted in a significant higher mortality within the first 10 days after the stroke while the total number of either dead or disabled patents was reduced when the thrombolytica where applied within six hour after stroke onset. This effects were mainly due to ICH. The broad use of thrombolytica for the treatment of stroke was therefore not recommended.

Even before, such results gave reason to some other authors mere sarcastic statement that stroke patients had the choice to either die or to survive disabled (SCRIP 1997: 2265, 26).

Nevertheless, so far the therapy with rt-PA is the only treatment of acute cerebral ischaemia approved by the Food and Drug Administration (FDA) in the USA. However, it is restricted to an application of rt-PA within three hours after the onset of stroke.

The approval of rt-PA was reached in 1996. Before, in the year 1995, first announcements about negative side effects of t-PA became known, which provide an explanatory basis for its dramatic effects when applied in stroke treatment outside the three hour time frame. Accordingly, micoglia cells and neuronal cells of the hippocampus produce t-PA which contributes to the glutamate mediated excitotoxicity. This is concluded from a comparative study on t-PA deficient and wild type mice when glutamate agonists were injected in their hippocampus, respectively. The t-PA deficient mice showed a significant higher resistance against external (inthrathecal) applied glutamate (Tsirka S E et al., Nature, Vol. 377, 1995, "Excitoxin-induced neuronal degeneration and seizure are mediated by tissue plasminogen activator"). These results were confirmed in 1998 when Wang et al. could prove nearly a double quantity of necrotic neuronal tissue in t-PA deficient mice when t-PA was injected intravenously. This negative effect of external t-PA on wild type mice was only approximately 33% (Wang et al., 1998, Nature, "Tissue plasminogen activator (t-PA) increases neuronal damage after focal cerebral ischaemia in wild type and t-PA deficient mice".)

Further results on the stimulation of excitotoxicity by t-PA were published by Nicole et al. In the beginning of 2001 (Nicole O., Docagne F Ali C; Margaill I; Carmeliet P; MacKenzie E T, Vivien D and Buisson A, 2001: The proteolytic activity of tissue plasminogen activator enhances NMDA receptor-mediated signaling; in: Nat Med 7, 59-64). They could prove that t-PA being released by depolarized cortical neurons could interact with the so called NR1 sub-unit of the glutamate receptor of the NMDA type leading to a cleavage of NR1. This increases the receptor's activity resulting in a higher tissue damage after glutamate agonist NMDA was applied. The NMDA agonist induced excitotoxicity.

Thus, t-PA exhibits a neurotoxic effect by activating the glutamate receptor of the NMDA type.

According to a further explanatory concept the neurotoxicity of t-PA results indirectly from the conversion of plasminogen in plasmin. According to this model plasmin is the effector of neurotoxicity (Chen Z L and Strickland S, 1997: Neuronal Death in the hippocampus is promoted by plasmin-catalysed degradation of laminin. Cell; 91, 917-925).

A summarizing outline of the time depending neurotoxic effect of t-PA is given in FIG. 5. Therein also the increased toxicity of the recombinant t-PA compared to endogenic t-PA becomes evident. This is probably due to rt-PA being able to enter into tissue in higher concentrations.

Despite its neurotoxic side effect and its increasing effect on the mortality t-PA was approved by FDA. This can only be explained by the lack of harmless and effective alternatives—thus it is due to a very pragmatic cost benefit analysis. Therefore, there is still a need for safe therapies. However, if they were still based on thrombolytica—in case it is not possible to find alternatives to thrombolysis—the problem of neurotoxicity has to be considered (see for example Wang et al. a.a.O.; Lewandowski and Barson 2001 a.a.O.).

Therefore, further examination of known thrombolytica including DSPA (Desmodus rotundus Plasminogen Activator) in order to develop new drugs for stroke was terminated although principally all thrombolytica are potentially suitable. Especially in case of DSPA its potential suitability for this medical indication was pointed out earlier (Medan P; Tatlisumak T; Takano K; Carano R A D; Hadley S J; Fisher M: Thrombolysis with recombinant Desmodus saliva plasminogen activator (rDSPA) in a rat embolic stroke model; in: Cerebrovasc Dis 1996: 6; 175-194 (4.sup.th International Symposium on Thrombolic Therapy in Acute Ischaemic Stroke), DSPA is a plasminogen activator with a high homology (resemblance) to t-PA. Therefore—and in addition to the disillusionment resulting from the neurotoxic side effects of t-PA—there were no further expectations, for DSPA being a suitable drug for stroke treatment.

Instead, recent strategies aiming to improve known thrombolytic treatments try to apply the thrombolytic substance no longer intravenously but intraarterially via a catheter directly close to the intravascular thrombus. First experience is available with recombinant produced urokinase. Thus, possibly, the necessary dose for thrombolysis and therewith negative side effects could be reduced. However, this application requires a high technical expenditure and is not available everywhere. Furthermore, the patient has to be prepared in a time consuming action. Time, however, is often limited. Thus, the preparation provides for an additional risk.

Presently, new concepts are directed to anticoagulants such as heparin, aspirin or ancrod, which is the active substance in the poison of the Malayan pit viper. Two further dinical trials examining the effects of heparin (International Stroke Trial (IST) and Trial of ORG 10172 in Acute Stroke Treatment (TOAST)) however, do not indicate a significant improvement of mortality or a prevention of stroke.

A further new treatment focuses neither on thrombus nor on blood thinning or anti coagulation but attempts to increase the vitality of cells damaged by the interruption of blood supply (WO 01/51613 A1 and WO 01/51614 A1). To achieve this antibiotics from the group of quinons, aminoglycosides or chloramphenicol are applied. For a, similar reason it is further suggested to begin with the application of citicholin directly after the onset of stroke. In the body, citicholin is cleaved to cytidine and choline. The cleavage products form part of the neuronal cell membrane and thus support the regeneration of damaged tissue (U.S. Pat. No. 5,827,832).

Recent research on safe treatment is based on the new finding that a part of the fatal consequences of stroke is caused only Indirectly by interrupted blood supply but directly to the excito- or neurotoxicity including over activated glutamate receptors. This effect is increased by t-PA (see above). A concept to reduce excitotoxicity is therefore to apply so called neuroprotectives. They can be used separately or in combination with fibrinolytic agents in order to minimize neurotoxic effects. They can lead to a reduced excitotoxicity either directly e.g. as a glutamate receptor antagonist or indirectly by inhibiting voltage dependent sodium or calcium channels (Jin-Mo Lee et al. a.a.O.).

A competitive inhibition (antagonistic action) of the glutamate receptor of NMDA type is possible e.g. with 2-amino-5-phosphonovalerate (APV) or 2-amino-5-phosphonoheptanoate (APH). A non competitive inhibition can be achieved e.g. by substances binding to the phencyclidine side of the channels. Such substances can be phencyclidine, MK801, dextrorphane or cetamine.

So far, treatments with neuroprotectives have not shown the expected success, possibly because neuroprotectives had to be combined with thrombolytic agents in order to exhibit their protective effects. This applies to other substances (see also FIG. 6).

Even a combination of t-PA and neuroprotective agents results only in a limited damage. Nevertheless, the disadvantageous neurotoxicity of the fibrinolytic agent as such is not avoided.

SUMMARY OF THE INVENTION

It is therefore an object of the present invention to provide a new therapeutic concept for the treatment of stroke in humans.

According to the invention the use of non-toxic plasminogen activating factors is suggested as outlined in claim 1 for the therapeutic treatment of stroke. Further advantageous uses are subject of independent claims, respectively, as well as of further dependent claims.

The central idea of the invention is the use of a plasminogen activator in the treatment of stroke, of which the mature enzyme exhibits an activity, which is selectively increased by fibrin manifold, namely more than the 650-fold.

The use of the plasminogen activators according to the invention is based on the following findings: Due to tissue damage in the brain caused by stroke the blood brain barrier is damaged or destroyed. Thus, fibrinogen circulating in the blood can enter into the neuronal tissue of the brain. There, it activates t-PA which—indirectly by activating the glutamate receptor or plasminogen—results in further tissue damage. In order to avoid this effect the invention suggests the use of a plasminogen activator which is highly fibrin selective and—as an inversion of the argument—has a reduced potential to be activated by fibrinogen. Thus, this plasminogen activator is not—or compared to t-PA at least substantially less-activated by fibrinogen entering from the blood into neuronal tissue as a result of damaged blood brain barrier, since t-PA's activator fibrin cannot enter the neuronal tissue due to its size. The plasminogen activators according to the invention therefore are non-neurotoxic.

BRIEF DESCRIPTION OF THE FIGURES

FIG. 9 shows the amino acid sequence of a modified uroquinase polypeptide (SEQ ID NO: 2).

FIG. 10 shows the amino acid sequence of a modified tissue plasminogen activator (SEQ ID NO: 1).

DETAILED DESCRIPTION OF THE INVENTION

Figure 1:
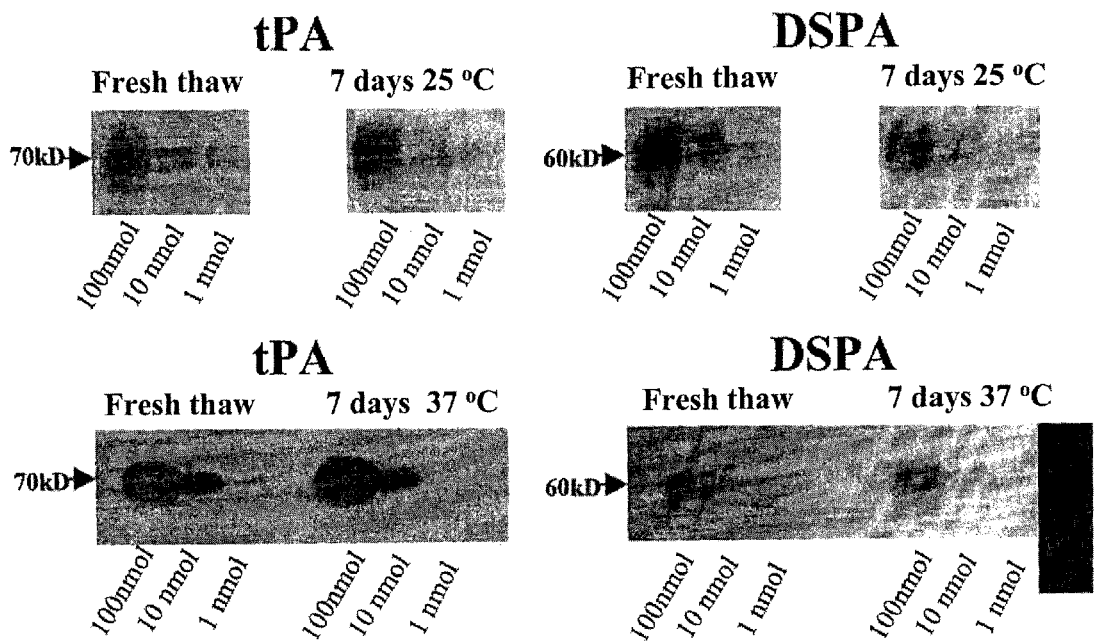
FIG. 1 shows results indicating that infusion of t-PA or DSPA disperses into the hippocampus of t-PA −/− mice and retains proteolytic activity. See Results section B.1 (p. 25).

According to a preferred embodiment of the invention, non-toxic plasminogen activators are used, which comprise at least one element of the so called cymogene triade. A comparable triade is known from the catalytic center of serine proteases of the chymotrypsine family consisting of three interacting amino acids aspartate 194, histidine 40 and serine 32. However, this triade does not exist in t-PA which belongs also to the family of chymotrypsine like serine proteases. Nevertheless, it is known, that the directed mutagenesis of native t-PA for the purpose of introducing at least one of the above amino acids at a suitable position results in a reduced activity of the pro-enzyme (single chain t-PA) and to an increased activity of the mature enzyme (double chain t-PA) in the presence of fibrin. Therefore, the introduction of at least one amino acid of the triade—or of an amino acid with the respective function in the triade—can increase the cymogenity of t-PA (i.e. the ratio between the activity of the mature enzyme an the activity of the pro-enzyme). As a result the fibrin specificity is remarkably increased. This is due to conformational interaction between the introduced amino acid residue and/or amino acid residues of the wild type sequence.

It is known that the mutagenesis of the native t-PA with substitution of Phe305 by His (F305H) and of Ala 292 by Ser (A92S) leads to a 20-fold increase of the cymogenity, whereas the variant F305H alone already leads to 5 times higher cymogenity (E L Madison, Kobe A, Gething M-J; Sambrook J F, Goldsmith E J 1993: Converting Tissue Plasminogen Activator to a Zymogen: A regulatory Triad of Asp-His-Ser; Science. 262, 419-421). In the presence of fibrin these t-PA mutants show an activity increase of 30.000 times (F305H) and 130.000 times (F305H, A292S) respectively. In addition these mutants comprise a substitution of Arg275 to R275E in order to prevent cleavage by plasmin at the cleavage site Aug275-Ile276, thereby converting the single chain t-PA to the double chain form. The mutant site 275E alone leads to a 6.900 fold increase of the fibrin specificity of t-PA (K Tachias, Madison E L 1995: Variants of Tissue-type Plasminogen Activator Which Display Substantially Enhanced Stimulation by Fibrin, in: Journal of Biological Chemistry 270, 31: 18319-18322).

The positions 305 and 292 of t-PA are homologous to the positions His40 and Ser32 of the known triade of the chymotryptic serine proteases. By the corresponding substitutions introducing histidine or respectively serine, these amino acids can interact with the aspartate 477 of t-PA resulting in a functional triade in the t-PA mutants (Madison et al., 1993).

These t-PA mutants can be used for the treatment of stroke according to the invention because they show no or—compared to wild type t-PA—a significantly reduced neurotoxicity due to their increased fibrin specificity. For the purpose of disclosure of the mentioned t-PA mutants F305H; F305H; A292S alone or in combination with R275E we incorporate the publications of Madison et al., (1993) and Tachias and Madison (1995) hereby are fully incorporated by reference.

The increase of fibrin specificity of plasminogen activators can alternatively be achieved by a point mutation of Asp194 (or an aspartate at a homologous position). Plasminogen activators belong to the group of serine proteases of the chymotrypsin family and therefore comprise the conserved amino acid Asp194, which is responsible for the stability of the catalytic active conformation of the mature proteases. It is known that Asp194 interacts with His40 in the cymogenic form of serine proteases. After the cymogene is activated by cleavage this specific interaction is interrupted and the side chain of the Asp194 rotates about 170.degree. in order to form a now salt bridge with Ile16. This salt bridge essentially contributes to the stability of the oxyanione pocket of the catalytic center of the mature serine proteases. It is also present in t-PA.

The introduction of a point mutation replacing Asp194 prima facie impedes the formation or respectively the stability of the catalytic confirmation of serine proteases. Despite this the mutated plasminogen activators show a significant increase of activity in the presence of their co-factor fibrin—especially in comparison to the mature wild type form—which can only be explained in a way that the interaction with fibrin allows a conformational change promoting catalytic activity (L Strandberg, Madison E L, 1995: Variants of Tissue-type Plasminogen Activator with Substantially Enhanced Response and Selectivity towards Fibrin co-factors, in: Journal of Biological Chemistry 270, 40: 2344-2349).

In conclusion, the Asp194 mutants of the plasminogen activators show a high increase of activity in presence of fibrin which enables their use according to the invention.

In a preferred embodiment according to the invention, a mutant t-PAIs used, in which Asp194 is substituted by glutamate (D194E) or respectively by asparagine (D194N). In these mutants the activity of t-PA is reduced 1 to 2000 fold in the absence of fibrin, whereas in the presence of fibrin, an increase of activity by a factor of 498.000 to 1.050.000 can be achieved. These mutants can further comprise a substitution of Arg15 to R15E, which prevents the cleavage of the single chain t-PA at the peptide bond Arg15-Ile18 by plasmin, leading to the double chain form of t-PA. This mutation alone increases the activation of t-PA by fibrin by the factor 12.000. For reasons of disclosure of the t-PA mutations at positions 194 and 15, the publications of Strandberg and Madison (1995) are fully incorporated by reference.

An increase of the fibrin dependency of plasminogen activators can also be achieved by the introduction of point mutations in the so called "autolysis loop". This element 18 known from trypsine; it can also be found as a homologous part in serine proteases and is especially characterized by three hydrophobic amino acids (Leu, Pro and Phe). The autolysis loop in plasminogen activators is responsible for the interaction with plasminogen. Point mutations in this area can have the effect that the protein-protein interaction between plasminogen and plasminogen activators cannot be effectively formed any longer. These mutations are only functionally relevant in the absence of fibrin. In the presence of fibrin, they, in contrast, are responsible for an increased activity of the plasminogen activators (K Song-Hua, Tachias K, Lamba D, Bode W, Madison E L, 1997: Identification of a Hydrophobic exocite on Tissue Type Plasminogen Activator That Modulates Specificity for Plasminogen, in: Journal of Biological Chemistry 272; 3, 1811-1816).

In a preferred embodiment t-PA is used showing point mutations in the positions 420 to 423. If these residues are substituted by directed mutagenesis this increases the fibrin dependency of t-PA is increased by a factor up to 61.000 (K Song-Hua et al.). Song-Hua et al. examined the point mutations L420A, L420E, S421G, S421E, P422A, P422G, P422E, F423A and F423E. These publications are fully incorporated by reference for disclosure of the use according to the invention.

According to a further advantageous embodiment a modified tissue plasminogen activator with an amino acid sequence according to SEQ ID NO. 1 (FIG. 10) is used. This modified t-PA differs from the wild type t-PA by the exchange of the hydrophobic amino acids in the position 420 to 423 in the autolysis loop as follows: His420. Asp421, Ala422 and Cys423. This t-PA preferentially contains a phenyl alanine at the position 194. Further the position 275 can be occupied by glutamate. Advantageously the position 194 is occupied by phenyl alanine.

Further, a modified urokinase can be used according to the invention. The urokinase according to the invention can comprise the amino acid sequence according to SEQ ID No. 2 (FIG. 9) in which the hydrophobic amino acids of the autolysis loop are substituted by Val420, Thr421. Asp422 and Ser423. Advantageously the urokinase is carrying an Ile275 and a Glu194. This mutant shows—in comparison to wild type urokinase—a 500-fold increased fibrin specificity.

Both mutants—urokinase as well as t-PA—were analyzed in semi quantitative tests and showed a increased fibrin specificity in comparison to the wild type t-PA.

The plasminogen activator (DSPA) from the saliva of the vampire bat (Desmodus rotundus) also shows a highly increased activity in the presence of fibrin—in specific a 10.000-fold increase. Thus it can be used preferentially according to the invention. The term DSPA comprises four different proteases, which fulfill an essential function for the vampire bat, namely an increased duration of bleeding of the wounds of pray (Cartwright, 1974). These four proteases (DSPAα1, DSPAα2, DSPAβ, DSPAγ) display a high similarity (homology) to each other and to the human t-PA. They also show similar physiological activities, leading to a common classification under the generic term OSPA. OSPA is disclosed in the patents EP 0 352 119 A1 and of U.S. Pat. Nos. 6,008,019 and 5,830,849 which are hereby fully incorporated by reference for purpose of disclosure.

DSPAα1 so far is the best analyzed protease from this group. It has an amino acid sequence with a homology greater than 72% in comparison to the known human t-PA amino acid sequence (Kratzschmar et al, 1991). However, there are two essential differences between t-PA and DSPA. Firstly all DSPA has full protease activity as a single chain molecule, since it is—in contrast to t-PA—not converted into a double chain form (Gardell et al., 1989; Kratzschmar et al., 1991). Secondly, the catalytic activity of DSPA is nearly absolutely dependent on fibrin (Gardell et al., 1989; 8ringmann et al., 1995; Toschie et al., 1998). For example the activity of DSPAα1 is increased 100.000 fold in the presence of fibrin whereas the t-PA activity is only increased 550 fold. In contrast, DSPA activity is considerably less strongly induced by fibrinogen, since it only shows a 7 to 9 fold increase (Bringmann et al., 1995). In conclusion, DSPA is considerably more dependent of fibrin and much more fibrin specific as wild type t-PA which is only activated 550-fold by fibrin.

Because of its fibrinolytic characteristics and the strong similarity to t-PA, DSPA is an interesting candidate for the development of a thrombolytic agent. Despite this, the therapeutic use of DSPA as a thrombolytic agent was restricted to the treatment of myocardinal infarction in the past, because—due to the contribution of t-PA to the glutamate induced neurotoxicity—no justified hopes existed, that a plasminogen activator which is related to t-PA could reasonably be used for a treatment of acute stroke.

Surprisingly it has been shown that DSPA has no neurotoxic effects even though it shows a high resemblance (homology) to t-PA and even though the physiological effects of the molecules are comparable to a large extent. The above conclusion led to the idea that DSPA after all may be successfully used as a thrombolytic agent for the therapy of stroke without causing severe risks of neuronal tissue damage. Especially interesting is the fact, that DSPA can also be used later than 3 hours after the onset of stroke symptoms.

A further teaching of the present invention that evolved from the above findings is the option to modify or produce further plasminogen activators in such a way that they reveal the essential characteristics of DSPA, especially the lack of the neurotoxicity of t-PA. The basis for this is the investigated relationship between structure and biochemical effects, making if possible to transform neurotoxic plasminogen activators into non-neurotoxic plasminogen activators and thereby to produce non-neurotoxic plasminogen activators on the basis of known or newly discovered neurotoxic plasminogen activators.

The new teaching is based on in vivo comparative examinations of the neurodegenerative effect of t-PA on one side and of DSPA on the other side which are performed by using the so called kainic acid model and a model for the examination of NMDA induced lesion of the striatum.

The kainic acid model (also kainic acid injury model) is based on the stimulation of the neurotoxic glutamate Cascade by the external application of kainic acid (KA) as an agonist of the glutamate receptor of the kainic acid type (KA type) and of the NMDA and AMPA glutamate receptors. Using a t-PA deficient mouse stem as an experimental model it was possible to show that the sensitivity of the laboratory animals against kainic acid only reached the level of wild type mice after a supplementary application of external t-PA. In contrast, an infusion of an equimolar concentration of DSPA under the same experimental conditions does not restore the sensitivity to kainic acid (KA). It was concluded that the neurotoxic effect of t-PA was not induced by DSPA. A summary of these results is shown in table 2.

TABLE 2

| | | Hippocampal length Intact (mm) | | |
|---|---|---|---|---|
| Treatment group | Number of animals | Contralateral side mean (SEM) | Ipsilateral side mean (SEM) | Percentage remaining |
| t-PA infusion (1.85 uM) + KA | 12 | 15.99 (0.208) | 3.63 (0.458) | 22.7* |
| DSPA infusion (1.85 uM) + KA | 11 | 16.07 (0.124) | 13.8 (0.579) | 85.87 |
| t-PA infusion (1.85 uM) + PBS | 3 | 16.75 (0.381) | 17.08 (0.363) | 101.97 |
| DSPA infusion (1.85 uM) + PBS | 3 | 15.75 (0.629) | 15.83 (0.363) | 100.50 |
| t-PA infusion (0.185 uM) + KA | 3 | 15.60 (0.702) | 5.07 (1.09) | 32.5 |
| DSPA infusion (18.5 uM) + KA | 3 | 16.06 (0.176) | 13.80 (1.22) | 85.93 |

*$P < 0.0001$

Figure 7:
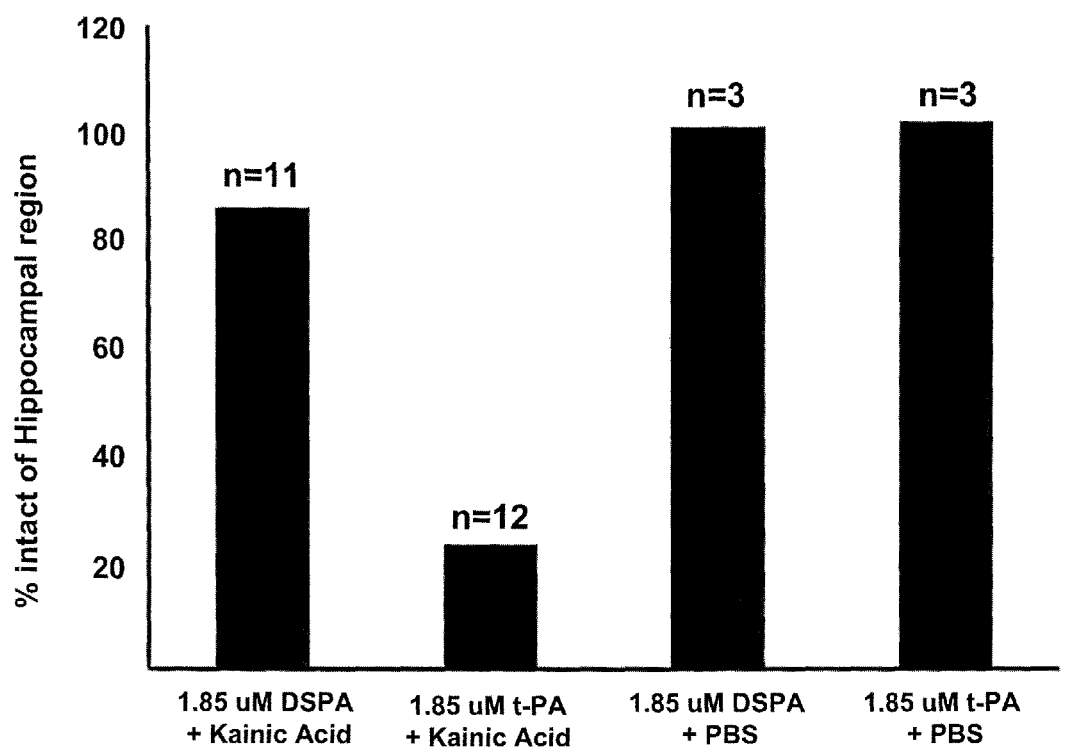
FIG. 7 shows results indicating that DSPA infused into t-PA −/− mice does not restore sensitivity to kainic acid-mediated neurodegeneration.
Figure 8:
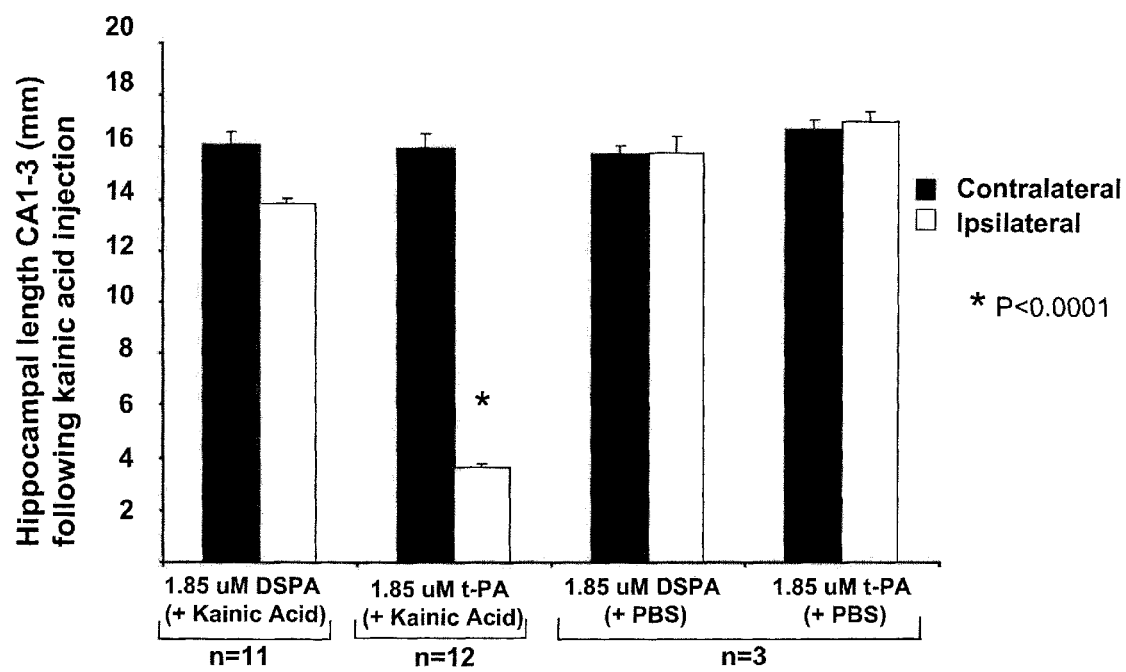
FIG. 8 also shows results indicating that DSPA infused into t-PA −/− mice does not restore sensitivity to kainic acid-mediated neurodegeneration.

Quantitative examinations based on this model revealed that even a 10-fold increase of the DSPA concentration could not restore the sensitivity of the t-PA deficient mice to the KA treatment whereas already a 10-fold lower t-PA concentration led to KA induced tissue damages. This leads to the conclusion that DSPA possesses an at least 100 fold lower neurotoxic potential as t-PA with respect to the stimulation of the neurodegeneration after KA treatment (see also FIGS. 7 and 8).

In the second model of neurodegeneration, the possible effects of t-PA as well as DSPA on the stimulation of the NMDA dependent neurodegeneration were compared to wild type mice. For this purpose, NMDA (as an agonist of the glutamate receptor of the NMDA type) was injected in Wild type mice alone or in combination with either t-PA or DSPA. This model allows the comparison of the effects of these proteases under conditions, which always lead to a neurodegeneration and to an influx of plasma proteins due to the break down of the blood brain barrier (Chen et al. 1999).

While working on this model the injection of NMDA led to reproducible lesions in the striatum of mice. The volume of lesions was increased by a combined injection of t-PA and NMDA by at least 50%. The co-injection with DSPAα1 in contrast did not lead to an increase or extension of the lesions caused by NMDA. Even in the presence of plasma proteins which can freely diffuse in the region of the lesion induced by NMDA, DSPA did not result in an increase neurodegeneration (see also table 3).

TABLE 3

| Treatment group | Number of wild-type mice | Mean lesion volume (mm$^3$) (SEM) | |
|---|---|---|---|
| NMDA alone | 8 | 1.85 (0.246) | |
| NMDA + t-PA | 8 | 3.987 (0.293)* | *$P < 0.0001$ |
| NMDA + DSPA | 8 | 1.656 (0.094)** | |
| t-PA alone | 3 | 0.20 (0.011) | |
| DSPA alone | 3 | 0.185 (0.016) | |

**Not significant

These results show that fibrin-free DSPA—in contrast to t-PA—behaves like an almost inert protease in the central nervous system of a mammal and also of a human—and therefore does not contribute to the neurotoxic effects caused by KA or NMDA. Despite of the prejudice against the therapeutic use of t-PA like proteins in stroke, this lacking neurotoxicity makes DSPA a suitable thrombolytic agent for the treatment of acute stroke.

First results of the clinical trials show the transferability of these results also for the treatment of stroke in humans. It was found that significant improvements can be achieved in patients after a successful perfusion (improvement by 8 points NIHSS or NIHSS score 0 to 1). Table 1 shows the data.

TABLE 1

| Patient | Baseline | NIHSS Post Tmt | Day 7 | Day 30 | Day 90 | sAEs |
|---|---|---|---|---|---|---|
| 1001 | 12 | 7 | 4 | 4 | * | Re-Infarction |
| 1002 | 8 | 9 | 2 | 0 | 0 | |
| 1003 | 8 | 10 | 12 | 10 | * | |
| 1004 | 8 | 4 | 2 | 0 | 0 | |
| 1005 | 11 | 11 | 4 | 5 | * | |
| 1006 | 9 | 7 | 1 | * | * | |
| 1007 | 14 | 6 | * | * | * | |
| 2001 | 19 | 20 | — | — | — | ICH, death |
| 2002 | 15 | 21 | — | — | — | ICH, death |
| 3001 | 8 | 7 | 6 | 5 | * | |
| 3002 | 15 | 16 | 9 | 8 | * | |
| 3003 | 10 | 19 | 21 | * | — | Death day 39 |

The lacking neurotoxicity of DSPA and of the other non-neurotoxic plasminogen activators (see above) offer the special advantage in stroke treatment that the use of these plasminogen activators—in contrast to the wild type t-PA—is not limited to a short maximum period of only 3 hours after the onset of stroke. In contrary, the treatment can be initiated later—for example after 8 hours or even later, since there is nearly no risk of stimulating excitotoxic responses. First clinical trials with DSPA prove a safe treatment of patients even in a time range of over 6 to 9 hours after the onset of stroke symptoms.

This option of a timely unlimited treatment with non-neurotoxic activators is of special importance, since it allows for the first time to treat patients with acute stroke symptoms safely even when diagnosis is delayed or the onset of the stroke cannot be determined with sufficient security. In the prior art, this group of patients was excluded from thrombolytic therapy with plasminogen activators due to unfavorable risk estimation. Consequently, an essential contra-indication for the authorized use of a thrombolytic agent for stroke is eliminated.

DSPA as well as further non-neurotoxic plasminogen activators show no tissue damaging side effects. However, it can be advantageous to apply them in combination with a neuroprotective agent for the treatment of stroke in order to limit the tissue damages induced by the glutamate occurring naturally in the human body. Neuroprotective agents inhibiting the glutamate receptor competitively or noncompetitively can be used. Useful combinations are e.g. with the known inhibitors of the glutamate receptors of the NMDA type, the kainic acid type or the quisqualate type, as for example APV, APH, phencyclidine, MK-801, dextrorphane or cetamine.

Further a combination with cations can be advantageous since cations, especially Zn-ions, block the cation channel regulated by the glutamate receptor and can therefore reduce neurotoxic effects.

In a further advantageous embodiment, non-neurotoxic plasminogen activators can be combined with at least one further therapeutic agent or with a pharmaceutically tolerable carrier. The combination with a therapeutic agent which supports the reduction of tissue damage by vitalizing the cells is especially advantageous, since it contributes to the regeneration of already damaged tissue or serves for the prevention of further stroke incidents. Advantageous examples are combinations with antibiotics as quinones, anticoagulants as heparin or hirudin as well as with citicholine or acetylsalicylic acid.

A combination with at least one thrombin inhibitor can also be advantageous. Preferentially, thrombomodulin and thrombomodulin analogs like for example solulin, triabin or pallidipin can be used. Further combinations with anti-inflammatory substances are advantageous, since they influence the infiltration by leucocytes.

Examples

Comparing Examinations of t-PA and DSPA are Methods:
1. Animals

Wild-type mice (c57/Black 6) and t-PA deficient mice (t-PA−/−mice) (c57/Black 6) (Carmeliet et al., 1994) were supplied by Dr. Peter Carmeliet, Leuven, Belgium.

2. Protein Extraction from Brain Tissue

The assessment of proteolytic activity in brain tissue following infusion of either t-PA or DSPAα1 was performed by zymographic analysis (Granelli-Piperno and Reich, 1974). After an infusion over a period of seven days into the hippocampus, mice were anaesthetised, then transcardially perfused with PBS and the brains removed. The hippocampus region was removed, transferred to eppendorf tubes and incubated in an equal volume (w/v) (approx. 30-50 µm) of 0.5% NP-40 lysis buffer containing no protease inhibitors (0.5% NP40, 10 mM Tris-HCl pH 7.4, 10 mM NaCL, 3 mM $MgCl_2$, 1 mM EDTA). The brain extracts were homogenized by means of a hand-held glass homogeniser and left on ice for 30 minutes. The samples were then centrifuged and the supernatant was removed. The amount of proteins present was determined (Bio-Rad-reagent).

3. Zymographic Analysis of the Proteases

The proteolytic activity in the samples and the brain tissue extracts was determined by zymographic analysis according to the method of Granelli, Piperno and Reich (1974). The samples with recombinant proteins (up to 100 nM) or the brain tissue extracts (20 µg) were subjected to a (10%) SDS-PAGE under non-reducing conditions. The gels were removed from the plates, washed in 1% triton X 100 for 2 hours and then overlaid onto an agarose gel containing polymerized fibrinogen and plasminogen (Granelli, Piperno and Reich, 1974). The gels were incubated at 37° C. in a humified chamber until proteolysed zones appeared.

4. Intra-Hippocampal Infusion of t-PA, DSPA and Subsequent Injection of Kainic Acid The kainic acid injury model was based on studies of Tsirka et al. (1995). The animals were injected intraperitoneally (I. p.) with atropine (4 mg/kg) and then anaesthetised with an i. p. injection of sodium pentobarbitol (70 mg/kg). Afterwards mice were placed in a stereotaxic frame and a micro-osmotic pump (Alzet model 1007D, Alzet Calif. USA) containing 100 µl of either PBS or recombinant human t-PA (0.12 mg/ml, 1.85 µM) or DSPAα.1 (1.85 µM) was implanted subcutaneously between the shoulder blades. The pumps were connected via sterile tubes to a brain cannula and inserted through a burr opening made through the skull at coordinates bregma −2.5 mm, midiolateral 0.5 mm and dorsoventral 1.6 mm in order to introduce the liquid near the midline. The cannula was fixed at the desired position and the pumps were allowed to infuse the respective solutions at a rate of 0.5 µl per hour for a total of 7 days.

Two days after infusion of the proteases the mice were reanaesthetised and again placed in the stereotaxic frame.

Afterwards 1.5 nmol of kainic acid (KA) in 0.3 μl PBS was injected unilaterally into the hippocampus. The coordinates were: bregma −2.5 mm, medial-lateral 1.7 mm and dorsoventral 1.6 mm. The excitotoxin (KA) was delivered for a duration of 30 seconds. After the kainic acid treatment the injection needle remained at these coordinates for further 2 minutes in order to prevent a reflux of the liquid.

5. Brain Processing Procedure

Five days after KA injection, the animals were anaesthetised and transcardially perfused with 30 ml PBS followed by 70 ml of a 4% paraformaldehyde solution, post fixed in the same fixative followed by incubation in 30% sucrose for further 24 hours. Coronal sections (40 μm) of the brain were then cut on a freezing microtome and either counter-stained with thionin (BDH, Australia) or processed for immunohistochemical examination as described below.

6. Quantification of Neuronal Loss within the Hippocampus

The quantification of neuronal loss in the CA1-CA3 hippocampal subfields was performed as previously described (Tsirka et al., 1995; Tsirka et al., 1996). Five consecutive parts of the dorsal hippocampus from all treatment groups were prepared taking care that the parts indeed comprised the place of the CA-injection and lesion area. The hippocampal subfields (CA1-CA3) of these sections were traced by means of camera lucida drawings of the hippocampus. The entire lengths of the subfields was measured by comparison to 1 mm standards traced under the same magnification. The lengths of tissue with viable pyramidal neurons (having normal morphology) and lengths of tissue devoid of neurons (no cells present, no thionin staining) was determined. The lengths, representing intact neurons and neuronal losses over each hippocampal subfield were averaged across sections and the standard deviations were determined.

7. Intra-Striatal NMDA Excitotoxic Lesions with or without t-PA or DSPA

Wild type mice (c57/Black 6) were anaesthetised and placed in a stereotaxic frame (see above). Mice then received an unilateral injection of 50 nmol NMDA in the left stratum, injected alone or in combination with either 46 μM rt-PA or 46 μM DSPAα1. As controls t-PA and DSPA were also injected alone (both at a concentration of 46 μM). The injection coordinates were: bregma −0.4 mm, midiolateral 2.0 mm and dorsoventral 2.5 mm. The solutions (1 μl total volume for all treatments) were transferred over a period of 5 minutes at a rate of 0.2 μl/min and the needle was left in place for further 2 minutes after the injection in order to minimize the reflux of fluid. After 24 hours the mice were anaesthetised and perfused transcardially with 30 ml PBS followed by 70 ml of a 4% paraformaldehyde solution, post fixed in the same fixative for 24 hours with followed by incubation in 30% sucrose for further 24 hours. Brains were then cut (40 μm) on a freezing microtome and mounted onto gelatin coated glass slides.

8. Quantification of the Lesion Volume following NMDA Injection

The quantification of the striatal lesion volume was performed using the method described by Callaway et al. (2000). Ten consecutive coronal sections spanning the lesioned area were prepared. The lesioned area was visualised using the Callaway method and the lesion volume was quantified by the use of a micro computer imaging device (MCIOD, Imaging Research Inc., Brock University, Ontario, Canada).

9. Immunohistochemistry

Immunohistochemistry was performed using standard methodologies. Coronal sections were immersed in a solution of 3% $H_2O_2$ and 10% methanol for 5 minutes followed by an incubation in 5% normal goat serum for 60 minutes. The sections were incubated over night either with an anti-GFAP antibody (1:1.000; Dako, Carpinteria, Calif., USA) for the detection of astrocytes, with an anti-MAC-1: antibody (1:1.000: Serotec. Raleigh, N.C., USA) for the detection of microglia or with polyclonal anti-DSPA antibodies (Schering AG, Berlin). After rinsing, the sections were incubated with the appropriate biotinylated secondary antibodies (Vector Laboratories, Burlingame, Calif., USA). This was followed by a final incubation with avidin/biotin-complex (Vector Laboratories, Burlingame, Calif., USA) for 60 minutes before visualisation with 3,3'-diaminebebcidine/ 0.03% $H_2O_2$. Sections were then mounted on gelatin coated slides, dried, dehydrated and coverslipped with permount.

B. Results

1. Infusion of t-PA or DSPA Disperses into the Hippocampus of t-PA −/− Mice and Retains Proteolytic Activity The initial experiments were designed to confirm that both DSPA and t-PA retain their proteolytic activity for the 7 day period of the infusion. To this end, aliquots of t-PA and DSPA (100 nmol) were incubated at 37° C. and at 30° C. for 7 days in a water bath. In order to determine the proteolytic activity, 5 fold serial dilutions of the probes were subjected to SPS-PAGE under non-reducing conditions and proteolytic activity was assessed by zymographic analyses. An aliquot of t-PA and DSPA which had been kept frozen for a period of 7 days was used as a control. As can be seen in FIG. 1 there was only a minor loss of DSPA or t-PA activity at an incubation with either 30° C. or 37° C. over this period of time.

Figure 2:
FIG. 2 shows results indicating that t-PA and DSPA activity is recovered in hippocampal extracts prepared from t-PA −/− mice following infusion. See Results section B.2 (p. 25).
Figure 2:
Figure 2:
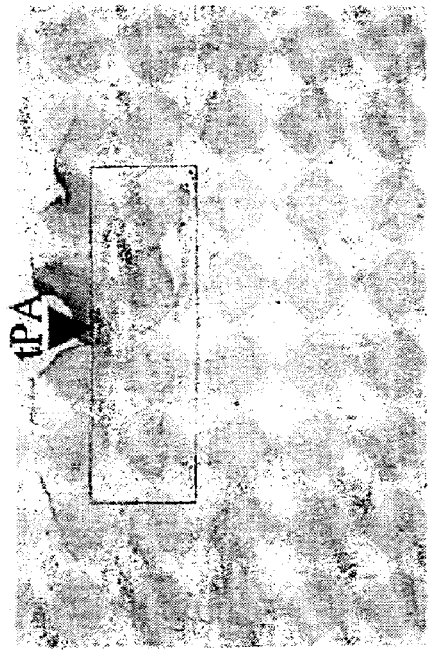
Figure 2:
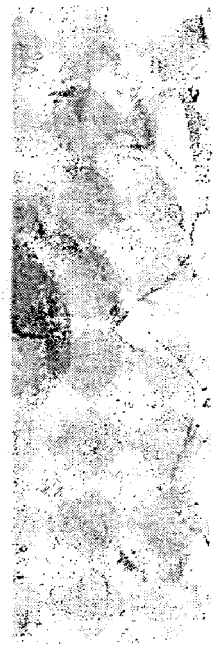
Figure 3A:
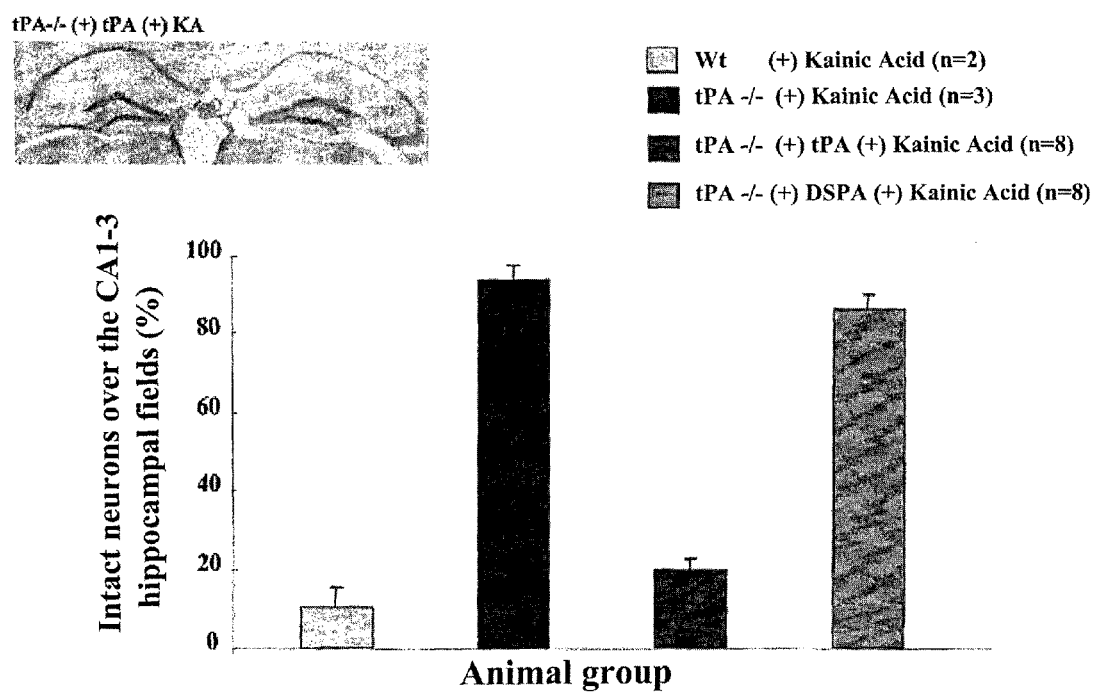
FIG. 3a shows neuronal survival in the hippocampus.
Figure 3B:
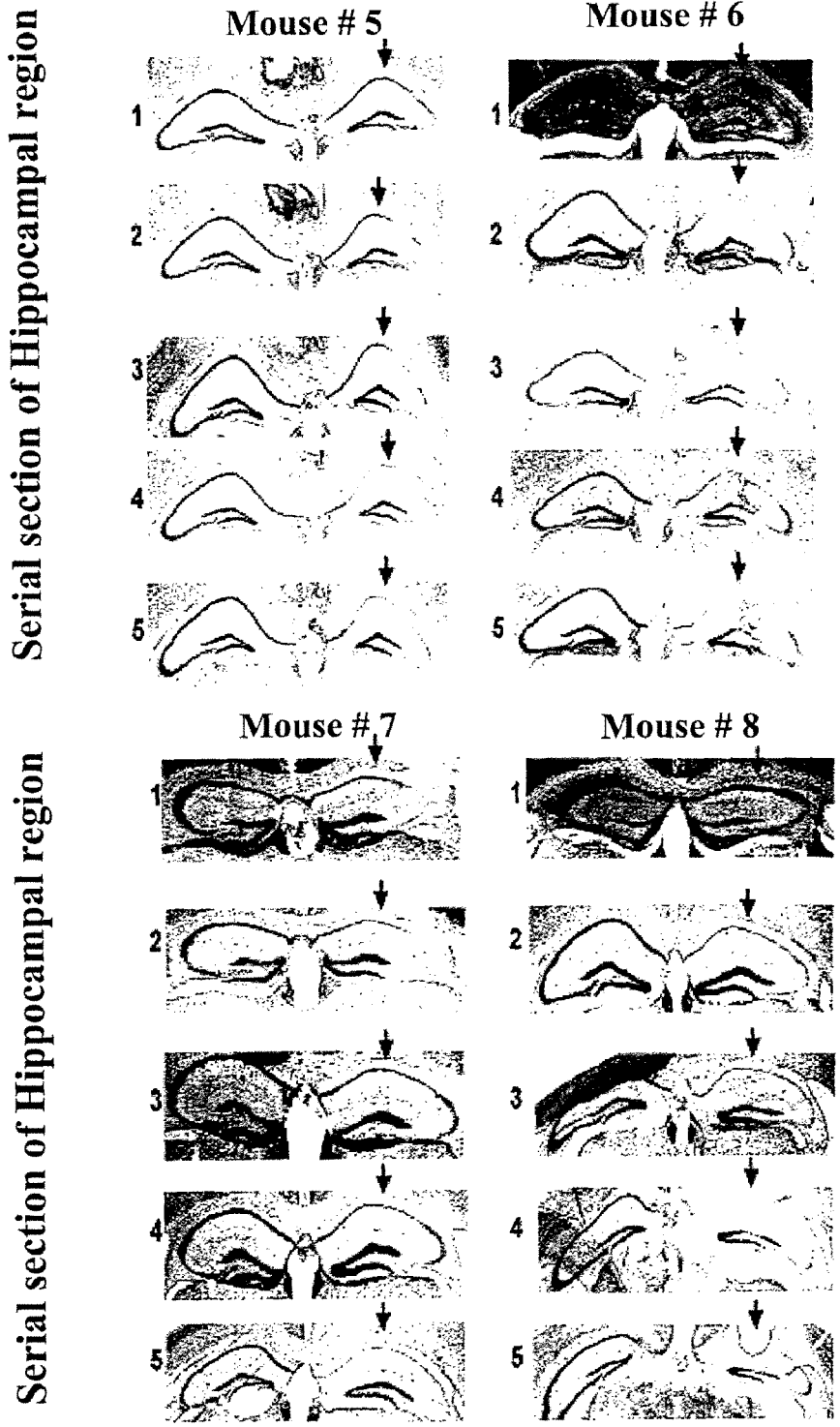
FIG. 3b shows serial sections of hippocampal regions for t-PA −/− mice infused with t-PA.

2. t-PA and DSPA Activity is Recovered in Hippocampal Extracts Prepared from t-PA −/− Mice Following Infusion First it had to be confirmed that the infused proteases were present in the brain of the infused animals and also retained their proteolytic activity while being in this compartment. To address this point, t-PA −/− were infused for seven days with either t-PA or DSPA (see above). Mice were then transcardially perfused with PBS and the brains removed. The ipsilateral and contralateral hippocampal regions were isolated as well as a region of the cerebellum (taken as a negative control). Tissue samples (20 μg) were subjected to SDS-PAGE and zymographic analysis according to the description in the methods section. As can be seen in FIG. 2, both t-PA and DSPA activities were detected in the ipsilateral region of the hippocampus, while some activity was also detected on the contralateral side. This indicates that the infused proteases not only retained their activity in the brain but had also diffused within the hippocampal region. As a control, no activity could be detected in the extract prepared from the cerebellum.

3. Immunohistochemical Assessment of DSPA

To further confirm that DSPA had indeed diffused into the hippocampal region, coronal brain sections of t-PA −/− mice were analysed immunohistochemically after DSPA infusion. DSPA-antigen was detected in the hippocampal region with the most prominent staining in the area of the infusion site. This result confirms that the infused IDPA is soluble and is indeed present in the hippocampus.

4. DSPA Infusion does not Restore Kainic-Acid Mediated Neurodegeneration in Vivo t-PA −/− mice are characteristically resistant to kainic acid (KA) mediated neurodegeneration. However, intrahippocampal infusion of rt-PA completely restores the sensitivity to KA-mediated injury. To determine whether DSPA could be substituted for t-PA in this model, t-PA −/− mice were infused intrahipocampically with either t-PA or DSPA using a mini-osmotic pump. For both groups 12 mice were tested. 2 days later the animals were injected with kainic acid and left to recover. 5 days later the animals were killed and the brains removed and prepared (see above). As controls, t-PA −/− mice were also infused with PBS prior to KA treatment (N=3).

Figure 4:
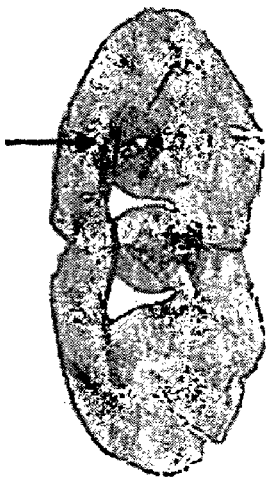
FIG. 4 shows results indicating that DSPA does not enhance NMDA-mediated neurodegeneration in the mouse striatum.
Figure 4:
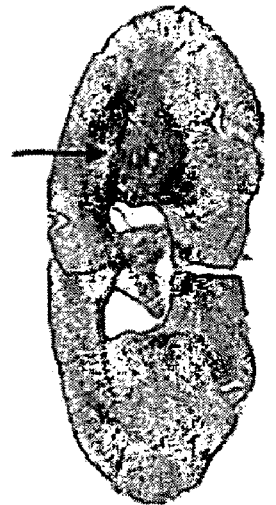
Figure 4:
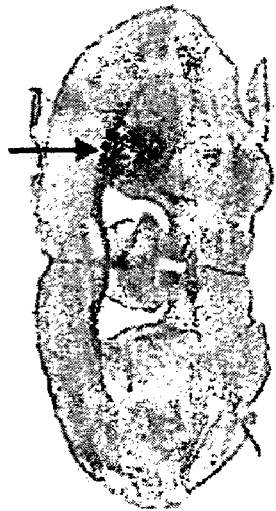
Figure 4:
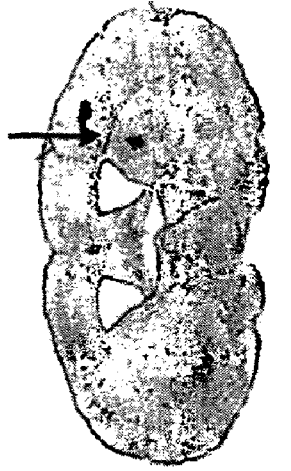
Figure 4:
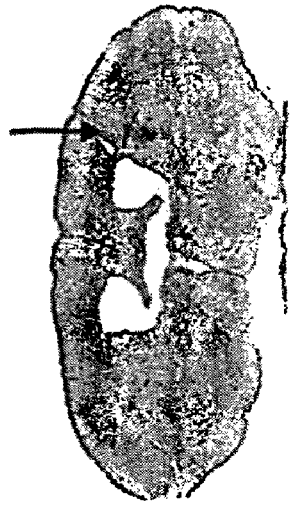
Figure 5:
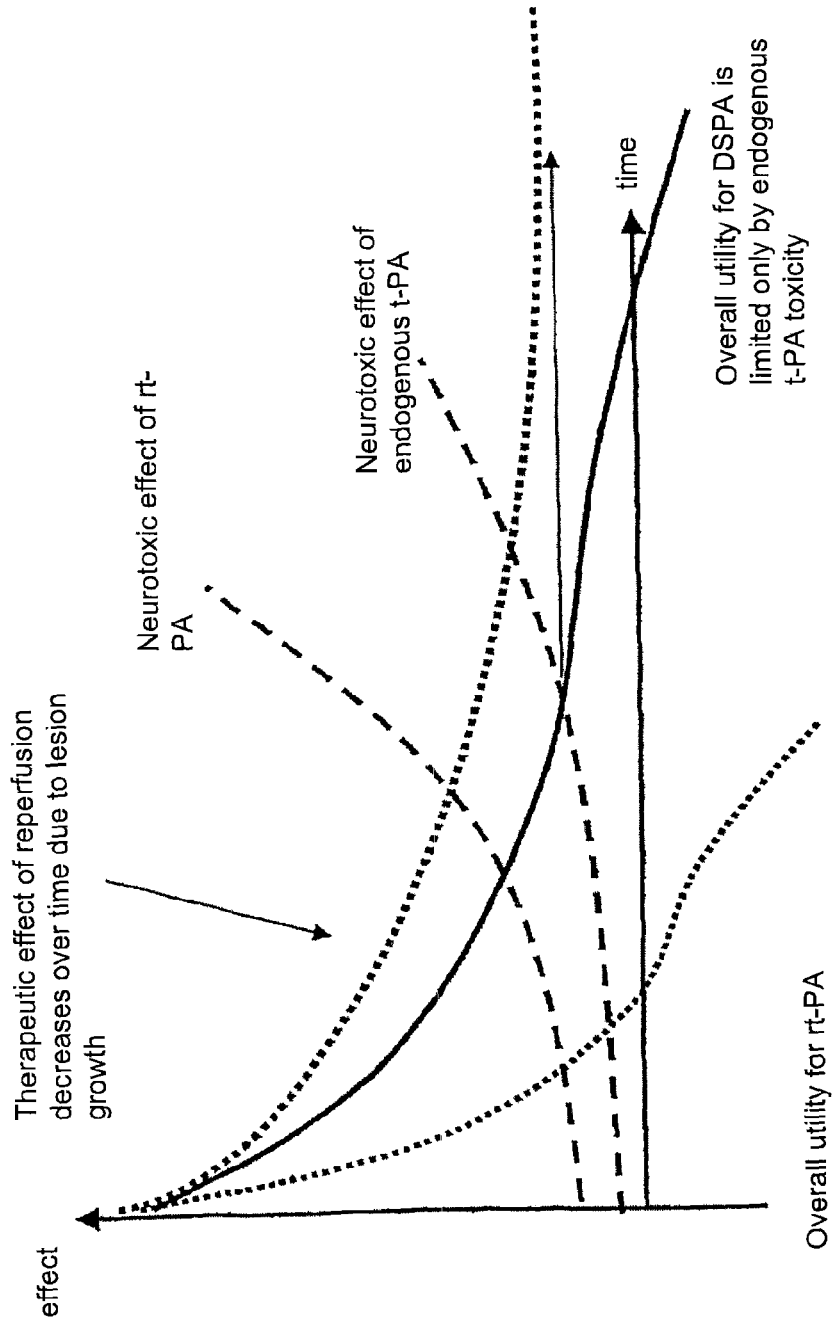
FIG. 5 shows the time-depending neurotoxic effect of t-PA and the increased toxicity of the recombinant t-PA compared to endogenic t-PA. See p. 7, 3rd full paragraph.
Figure 6:
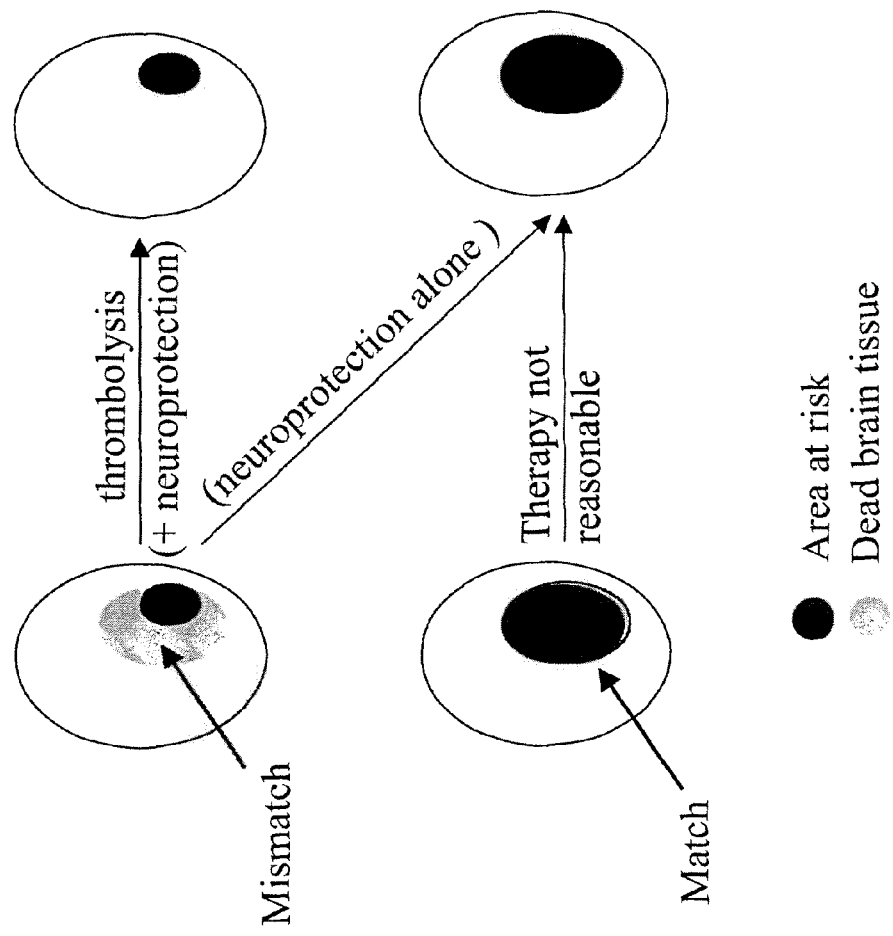
FIG. 6 shows salvageable tissue as a requirement for a successful treatment.

Coronal brain sections were prepared and the neurons detected by Nissl staining As shown in FIG. 4, t-PA −/− mice infused with PBS were resistant to subsequent challenge with KA. However, infusion of recombinant t-PA restored sensitivity to KA treatment. In contrast, infusion of the same concentration of DSPA into the hippocampal region did not alter the sensitivity of the animals to KA.

A quantitation of those results was based on data obtained from 12 mice in each group. In 2 of the 12 mice infused with DSPA a small extend of neurodegeneration was observed. The reason for that in unclear and possibly not related to the presence of DSPA. The combined data consider this minor effect that was observed in the case of these 2 animals. All 12 mice treated with t-PA were sensitive against the KA treatment. These results show that in case of an infusion of tPA or DSPAα1 in equimolar concentrations only the administering of t-PA led to the restoration of sensitivity to KA induced neurodegeneration.

5. DSPA Infusion does not Result in Microglial Activation

The restauration of the KA sensitivity of the t-PA −/− mice caused by a t-PA infusion also results in a microglia activation (Rogove et al., 1999). To assess the degree of microglial activation following t-PA or DSPA infusion and subsequent KA treatment, coronal sections of mice were subjected to an immunohistochemical staining for activated microglia cells using the Mac-1 antibody. The resaturation of KA sensitivity following t-PA infusion resulted in a clear increase in Mac-1 positive cells. This was not observed in mice infused with DSPA. Hence, the presence of DSPA does not result in the activation of microglia cells following KA treatment 6. Titration of DSPA and t-PA in the Mice Hippocampus Region.

The concentration of t-PA used for the infusion was based on the concentration described by Tsirka et al. (1995) (100 μl of 0.12 mg/ml [1.85 μM]). The KA-injury experiments were repeated using a 10-fold lower of t-PA (0.185 μM) and a 10-fold higher amount of DSPA (18.5 μM). The lower t-PA concentration was still able to restore the sensitivity to KA treatment (n=3). Of special interest was the finding that the infusion of 10 fold increased DSPA concentration only caused a little neuronal loss following KA treatment. These data strongly point out that DSPA does not lead to an increase of sensitivity to KA.

7. Effect of t-PA and DSPA on NMDA-Dependent Neurodegeneration in Wild Type Mice The effects of t-PA and DSPA were also examined in a model of neurodegeneration in wild type mice. The injection of t-PA in the striatum of these mice provably led to an increase of the neurodegenerative effects caused by the glutamate analogue NMDA (Nicole et al., 2001).

NMDA was injected into the striatal region of wild type mice in the presence of t-PA or DSPA (each 46 μM) with a total volume of 1 μl. After 24 hours the brains were removed and the size of the lesions was quantified according to the Callaway method (Callaway et al., 2000) (see above). As can be seen in FIG. 4, injection of NMDA alone caused a reproducible lesion in all treated mice (N=4). When t-PA and NMDA were applied together, the size of the lesions was increased about 50% (P<0.01, n=4): In a clear contrast the co-injection of NMDA and the same concentration of DSPA did not lead to an increase in lesion size compared to NMDA alone.

Injection of t-PA or DSPA alone did not lead to a detectable neurodegeneration. The lacking effect of t-PA when being administered alone is consistent with the results of Nicole et al. (2001). These data show that the presence of DSPA does not increase neurodegeneration even during a neurodegenerative event.

In order to confirm that the injection of DSPA had indeed spread into the hippocampal region, immunohistochemistry was performed on coronal sections by use of the DSPA antibody. The examination showed that DSPA did indeed enter the striatal region.

Kinetic Analysis of the Plasminogen Activation by Indirect Chromogen Test

Indirect chromogen tests of the t-PA activity were performed using the substrate Lys-plasminogen (American Diagnostica) and spectrocyme PL (American Diagnostics) according to Madisan E. L., Goldsmith E. J., Gerard R. D., Gething M.-J., Sambrook J. F. (1989) Nature 339 721-724; Madison E. L O., Goldsmith E. J., Gething M. J., Sambrook J. F. and Bassel-Duby R. S. (1990) Proc. Natl. Acad. Sci. U.S.A 87, 3530-3533 as well as Madison E. L., Goldsmith E. J., Gething M. J., Sambrook J. F. and Gerard R. D. (1990) J. Biol. Chem. 265, 21423-21426. Tests were performed both in the presence and absence of the co-factor DESAFIB (American Diagnostica), DESAFIB is a preparation of soluble fibrin monomeres gained by the cleavage of highly pure human fibrinogen with the protease batroxobin. Batroxobin cleaves the $Arg^{15}$-$Gly.^{17}$-binding in the A.α.-chain of fibrinogen and thereby releases fibrinopeptid A. The resulting des-AA-fibrinogen representing fibrin I monomers is soluble in the absence of the peptide Gly-Pro-Arg-Pro. The concentration of Lys-plasminogen was varied from 0.0125 up to 0.2 μM in the presence of DESAFIB and from 0.9 to 16 μM in absence of the co-factor.

Indirect Chromogen Tests in the Presence of Different Stimuli.

Indirect chromogen standard tests were performed according to the publications cited above. Probes of 100 μl total volume containing 0.25-1 ng enzyme, 0.2 μM Lys-plasminogen and 0.62 mM spectrocyme PL were used. The tests were performed either in the presence of buffer, 25 μg/ml DESAFIB, 100 μg/ml cyanogen bromide fragments of fibrinogen (American Diagnostica) or 100 μg/ml of the stimulatory 13 amino acid peptide P368. The analysis were performed in microtiter-plates and the optic density was determined at a wave length of 405 nm every 30 seconds for 1 hour in a "Molecular Devices Thermomax". The reaction temperature was 37° C.

The invention claimed is:

1. A method for treating ischemic stroke comprising administering to a human in need of such treatment, a therapeutically effective amount of a composition consisting essentially of *Desmodus rotundus* Salivary Plasminogen Activator alpha 1 (DSPAα1), wherein the DSPAα1 is recombinantly produced; and wherein the composition is administered intravenously more than 3 hours after onset of stroke symptoms.

2. The method according to claim 1, wherein said composition is administered to the human within 6 hours after the onset of stroke symptoms.

3. The method according to claim 1, wherein said composition is administered to the human within 9 hours after the onset of stroke symptoms.

4. The method according to claim 1, wherein the composition further comprises one or more pharmaceutically acceptable excipients.

5. The method according to claim 2, wherein the composition further comprises one or more pharmaceutically acceptable excipients.

6. The method according to claim 3, wherein the composition further comprises one or more pharmaceutically acceptable excipients.

7. The method of claim 1, wherein said composition is administered to the human 6 to 9 hours after the onset of stroke symptoms.

8. The method of claim 1, wherein said composition is administered to the human more than 3 hours to 9 hours after the onset of stroke symptoms.

9. The method of claim 1, wherein said composition is administered to the human more than 3 hours to 6 hours after the onset of stroke symptoms.

* * * * *

SEQUENCE LISTING

<160> NUMBER OF SEQ ID NOS: 2

<210> SEQ ID NO 1
<211> LENGTH: 476
<212> TYPE: PRT
<213> ORGANISM: Artificial
<220> FEATURE:

<223> OTHER INFORMATION: Modified t-PA

<400> SEQUENCE: 1

```
Met Val Asn Thr Met Lys Thr Lys Leu Leu Cys Val Leu Leu Leu Cys
1               5                   10                  15

Gly Ala Val Phe Ser Leu Pro Arg Gln Glu Thr Tyr Arg Gln Leu Ala
            20                  25                  30

Arg Gly Ser Arg Ala Tyr Gly Val Ala Cys Lys Asp Glu Ile Thr Gln
        35                  40                  45

Met Thr Tyr Arg Arg Gln Glu Ser Trp Leu Arg Pro Glu Val Arg Ser
    50                  55                  60

Lys Arg Val Glu His Cys Gln Cys Asp Arg Gly Gln Ala Arg Cys His
65                  70                  75                  80

Thr Val Pro Val Lys Ser Cys Ser Glu Pro Arg Cys Phe Asn Gly Gly
                85                  90                  95

Thr Cys Gln Gln Ala Leu Tyr Phe Ser Asp Phe Val Cys Gln Cys Pro
            100                 105                 110

Glu Gly Phe Ala Gly Lys Cys Cys Glu Ile Asp Thr Arg Ala Thr Cys
        115                 120                 125

Tyr Glu Asp Gln Gly Ile Ser Tyr Arg Gly Thr Trp Ser Thr Ala Glu
    130                 135                 140

Ser Gly Ala Glu Cys Thr Asn Trp Asn Ser Ser Ala Leu Ala Gln Lys
145                 150                 155                 160

Pro Tyr Ser Gly Arg Arg Pro Asp Ala Ile Arg Leu Gly Leu Gly Asn
                165                 170                 175

His Asn Tyr Cys Arg Asn Pro Asp Arg Asp Ser Lys Pro Trp Cys Tyr
            180                 185                 190

Val Phe Lys Ala Gly Lys Tyr Ser Ser Glu Phe Cys Ser Thr Pro Ala
        195                 200                 205

Cys Ser Ser Thr Cys Gly Leu Arg Gln Tyr Ser Gln Pro Gln Phe His
    210                 215                 220

Ser Thr Gly Gly Leu Phe Ala Asp Ile Ala Ser His Pro Trp Gln Ala
225                 230                 235                 240

Ala Ile Phe Ala Lys His Arg Arg Ser Pro Gly Glu Arg Phe Leu Cys
                245                 250                 255

Gly Gly Ile Leu Ile Ser Ser Cys Trp Ile Leu Ser Ala Ala His Cys
            260                 265                 270

Phe Gln Glu Arg Phe Pro Pro His Leu Thr Val Ile Leu Gly Arg
        275                 280                 285

Thr Tyr Arg Val Val Pro Gly Glu Glu Gln Lys Phe Glu Val Glu
    290                 295                 300

Lys Tyr Ile Val His Lys Glu Phe Asp Asp Thr Tyr Asp Asn Asp
305                 310                 315                 320

Ile Ala Leu Leu Gln Leu Lys Ser Asp Ser Ser Arg Cys Ala Gln Glu
                325                 330                 335

Ser Ser Val Val Arg Thr Val Cys Leu Pro Pro Ala Asp Leu Gln Leu
            340                 345                 350

Pro Asp Trp Thr Glu Cys Glu Leu Ser Gly Tyr Gly Lys His Glu Ala
        355                 360                 365

Leu Ser Pro Phe Tyr Ser Glu Arg Leu Lys Glu Ala His Val Arg Leu
    370                 375                 380

Tyr Pro Ser Ser Arg Cys Thr Ser Gln His Leu Leu Asn Arg Thr Val
385                 390                 395                 400

Thr Asp Asn Met Leu Cys Ala Gly Asp Thr Arg Ser Gly Gly Pro Gln
```

```
                         405                 410                 415
Ala Asn Leu His Asp Ala Cys Gln Gly Asp Ser Gly Gly Pro Leu Val
            420                 425                 430

Cys Leu Asn Asp Gly Arg Met Thr Leu Val Gly Ile Ile Ser Trp Gly
            435                 440                 445

Leu Gly Cys Gly Gln Lys Asp Val Pro Gly Val Tyr Thr Lys Val Thr
            450                 455                 460

Asn Tyr Leu Asp Trp Ile Arg Asp Asn Met Arg Pro
465                 470                 475

<210> SEQ ID NO 2
<211> LENGTH: 477
<212> TYPE: PRT
<213> ORGANISM: Artificial
<220> FEATURE:
<223> OTHER INFORMATION: Modified Urokinase

<400> SEQUENCE: 2

Met Val Asn Thr Met Lys Thr Lys Leu Leu Cys Val Leu Leu Leu Cys
1               5                   10                  15

Gly Ala Val Phe Ser Leu Pro Arg Gln Glu Thr Tyr Arg Gln Leu Ala
            20                  25                  30

Arg Gly Ser Arg Ala Tyr Gly Val Ala Cys Lys Asp Glu Ile Thr Gln
        35                  40                  45

Met Thr Tyr Arg Arg Gln Glu Ser Trp Leu Arg Pro Glu Val Arg Ser
50                  55                  60

Lys Arg Val Glu His Cys Gln Cys Asp Arg Gly Ser Asn Glu Leu His
65                  70                  75                  80

Gln Val Pro Ser Asn Ser Cys Asp Glu Pro Arg Cys Leu Asn Gly Gly
                85                  90                  95

Thr Cys Val Ser Asn Lys Tyr Phe Ser Ile His Trp Cys Asn Cys Pro
            100                 105                 110

Lys Lys Phe Gly Gly Gln His Cys Glu Ile Asp Lys Ser Lys Thr Cys
        115                 120                 125

Tyr Glu Gly Asn Gly His Phe Tyr Arg Gly Lys Ala Ser Thr Asp Thr
    130                 135                 140

Met Gly Arg Pro Cys Leu Pro Trp Asn Ser Ala Thr Val Leu Gln Gln
145                 150                 155                 160

Thr Tyr His Ala His Arg Ser Asp Ala Leu Gln Leu Gly Leu Gly Lys
                165                 170                 175

His Asn Tyr Cys Arg Asn Pro Asp Asn Arg Arg Arg Pro Trp Cys Tyr
            180                 185                 190

Val Gln Val Gly Leu Lys Pro Leu Val Gln Glu Cys Met Val His Asp
        195                 200                 205

Cys Ala Asp Phe Gln Cys Gly Gln Lys Thr Leu Arg Glu Pro Arg Phe
    210                 215                 220

His Ser Thr Gly Gly Glu Phe Thr Thr Ile Glu Asn Gln Pro Trp Phe
225                 230                 235                 240

Ala Ala Ile Tyr Arg Arg His Arg Gly Gly Ser Val Thr Tyr Val
                245                 250                 255

Cys Gly Gly Ser Leu Met Ser Pro Cys Trp Val Ile Ser Ala Thr His
            260                 265                 270

Cys Phe Ile Asp Tyr Pro Lys Lys Glu Asp Tyr Ile Val Tyr Leu Gly
        275                 280                 285

Arg Ser Arg Leu Asn Ser Asn Thr Gln Gly Glu Met Lys Phe Glu Val
    290                 295                 300
```

-continued

```
Glu Asn Leu Ile Leu His Lys Asp Tyr Ser Ala Asp Thr His His Asn
305                 310                 315                 320

Asp Ile Ala Leu Leu Lys Ile Arg Ser Lys Glu Gly Arg Cys Ala Gln
                325                 330                 335

Pro Ser Arg Thr Ile Gln Thr Ile Cys Leu Pro Ser Met Tyr Asn Asp
            340                 345                 350

Pro Gln Phe Gly Thr Ser Cys Glu Ile Thr Gly Phe Gly Lys Glu Asn
        355                 360                 365

Ser Thr Asp Tyr Leu Tyr Pro Glu Gln Leu Lys Met Thr Val Val Lys
    370                 375                 380

Leu Ile Ser His Arg Glu Cys Gln Gln Pro His Tyr Tyr Gly Ser Glu
385                 390                 395                 400

Val Thr Thr Lys Met Leu Cys Ala Ala Asp Pro Gln Trp Lys Glu Ile
                405                 410                 415

Tyr Pro Asn Val Thr Asp Ser Cys Gln Gly Asp Ser Gly Gly Pro Leu
            420                 425                 430

Val Cys Ser Leu Gln Gly Arg Met Thr Leu Thr Gly Ile Val Ser Trp
        435                 440                 445

Gly Arg Gly Cys Ala Leu Lys Asp Lys Pro Gly Val Tyr Thr Arg Val
    450                 455                 460

Ser His Phe Leu Pro Trp Ile Arg Ser His Thr Lys Leu
465                 470                 475
```